United States Patent [19]

Bounous et al.

[11] Patent Number: 5,290,571
[45] Date of Patent: * Mar. 1, 1994

[54] BIOLOGICALLY ACTIVE WHEY PROTEIN CONCENTRATE

[75] Inventors: Gustavo Bounous, Montreal; Phil Gold, Westmount; Patricia A. L. Kongshavn, St. Lambert, all of Canada

[73] Assignee: Immunotec Research Corporation, Ltd., Quebec, Canada

[*] Notice: The portion of the term of this patent subsequent to Jul. 27, 2010 has been disclaimed.

[21] Appl. No.: 417,246

[22] Filed: Oct. 4, 1989

Related U.S. Application Data

[63] Continuation-in-part of Ser. No. 289,971, Dec. 23, 1988, abandoned, and a continuation of Ser. No. 188,271, Apr. 28, 1988, abandoned.

[51] Int. Cl.⁵ .............................................. A61K 35/20
[52] U.S. Cl. ....................................... 424/535; 514/2; 514/21; 514/251; 514/276; 514/885; 530/365; 530/833; 426/72
[58] Field of Search .................. 514/2, 21, 251, 276, 514/885; 530/365, 833; 424/535; 426/72

[56] References Cited

U.S. PATENT DOCUMENTS

| | | | |
|---|---|---|---|
| 4,043,990 | 8/1977 | Melachouris | 530/365 |
| 4,485,040 | 11/1984 | Roger et al. | 530/833 |
| 4,497,836 | 2/1985 | Marquardt et al. | 426/239 |
| 4,784,685 | 11/1988 | Meister | 504/110 |

FOREIGN PATENT DOCUMENTS

| | | |
|---|---|---|
| 1136919 | 7/1982 | Canada. |
| 0022696 | 1/1981 | European Pat. Off.. |
| 239722 | 10/1987 | European Pat. Off.. |
| 2296428 | 9/1976 | France. |
| 87/00036 | 7/1987 | PCT Int'l Appl.. |
| 1495940 | 12/1977 | United Kingdom. |

OTHER PUBLICATIONS

Baricelli, G. C.: De seri facultatibus, et usu, opusculum secundum, Scorriggium, Publ. Naples, Italy, pp. 105–147, 1603.

Cantani, A.: Latte e siero di latte in-Materia medica e terapeutica-vol. 1-Vallardi F. Publ., Milano, Italy, p. 385, 1869.

Hoffman, K. F.: Zur geschichte der molkenkuren, insbesondere im 17, 18 und 19 Jahrhundert. Med. Monatschr 15: 411–416, 1961.

Barness, L. A., et al.: Progress of premature infants fed a formula containing demineralized whey. Pediatrics, Jul. 1963, pp. 52–55.

Raiha, N. C. R., et al.: Milk protein quantity and quality in low birth weight infants I. Metabolic responses and effects on growth. Pediatrics 57:659–674, 1976.

Rassin D. K. et al.: Milk protein quantity and quality in low birth weight infants. J. Pediat. 90: 356–360, 1977.

Berger, H. M., et al: Curd and whey proteins in the nutrition of low birth weight babies. Arch. Dis. in Child. 54: 98–104, 1979.

Mietens, C. et al.: Treatment of infantile E. coli gastroenteritis with specific bovine anti-E. coli milk immunoglobulins. Europ. J. Pediatr. 132: 239–252, 1979.

(List continued on next page.)

Primary Examiner—Douglas W. Robinson
Assistant Examiner—Jean C. Witz
Attorney, Agent, or Firm—John P. White

[57] ABSTRACT

The present invention is concerned with a whey protein composition comprising a suitable concentration of whey protein concentrate wherein the whey protein concentrate contains proteins which are present in an essentially undenatured state and wherein the biological activity of the whey protein concentrate is dependent on the overall amino acid and small peptides pattern resulting from the contribution of all its protein components and a method of producing said whey protein composition. The invention also relates to several applications of said composition.

13 Claims, 9 Drawing Sheets

OTHER PUBLICATIONS

Bounous, G. et al: Influence of dietary lactalbumin hydrolysate on the immune system of mice and resistance to Salruonellosis. J. Infect. Dis. 144: 281, 1981.

Williamson, J. M. et al: Stimulation of hepatic gluathione formation by administration of L-2-oxothiazolidine-4-carboxylate, a 5-oxo-L-prolinase substrate. Proc. Natl. Acad. Sci. (USA) 78: 936-939, 1981.

Williamson, J. M. et al: Intracellular cysteine delivery system that protects against toxicity by promoting GSH synthesis. Proc. Natl. Acad. 79: 6246-6249, 1982.

Bounous, G. et al.: Influence of dietary proteins on the immune system of mice. J. Nutr. 112: 1747-1755, 1982.

Birt, D. et al: Nutritional evaluation of three dietary levels of lactalbumin throughout the lifespan of two generations of Syrian hamsters. J. Nutr. 112: 2151-2160, 1982.

Birt, D. F., et al.: Survival of hamsters fed graded levels of two protein sources. Lab. Animal Sci. 32: 363-366, 1982.

Bounous, G. et al.: Influence of dietary protein type on the immune system of mice. J. Nutr. 113: 1415-1421, 1983.

Volz, V. R. et al: Growth and plasma amino acid concentrations in term infants fed either whey-predominant formula or human milk. J. Pediatr. 102: 27-31, 1983.

Esterela, J. M. et al: The effect of cysteine and N-acetylcysteine on rat liver glutathione. Biochem. Pharmacol. 32: 3483-3485, 1983.

Anderson, M. E. et al: Transport and direct utilization of gamma-glutamylcysteine for glutathione synthesis. Proc. Natl. Acad. Sci. (USA) 80: 707-711, 1983.

Puri, R. N. et al: Transport of glutathione as gamma--glutamylcysteinyl-glycylester into liver and kidney. Proc. Natl. Acad. Sci. (USA) 80: 5258-5260, 1983.

Janas, L. M. et al: Indices of protein metabolism in term infants fed human milk, whey predominant formula or cow's milk formula. Pediatrics 75: 775-784, 1985.

Darling, P. et al: Protein quality and quantity in preterm infants receiving the same energy intake. Am. J. Dis. of Child. 139: 186-190, 1985.

Bounous, G. et al: Mechanism of altered $\beta$-cell response induced by changes in dietary protein type in mice. J. Nutr. 115: 1409-1417, 1985.

Shenai, J. P. et al: Nutritional balance studies in very low birth weight infants: role of whey formula. J. Ped. Gastr. and Nutr. 5: 428-433, 1986.

Lauterburg, B. H. et al: Therapeutic doses of acetaminophen stimulate the turnover of cysteine and glutathione in man. J. Hepat. 4: 206-211, 1987.

Bounous, G., et al: Dietary whey protein inhibits the development of dimethylhydrazine induced malignancy. Clin. Invest. Med. 11: 213-217, 1988.

Tacket, C. O. et al: Protection by milk immunoglobulin concentrate against oral challenge with enterotoxigenic *Escherichia Coli*. New Engl. J. Med. 318: 1240-1243, 1989.

Taylor, Y. C. et al: Elevation of intracellular glutathione levels following depletion and its relationship to protection against radiation and alkylating agents. Pharmacology Ther. 39: 293-299, 1988.

White, C. W. et al: Hypoxia increases glutathione redox cycle and protects rat lungs against oxidants. J. Appl. Physiol 65: 2607-2616, 1988.

Bounous, G. et al: The immunoenhancing property of dietary whey protein concentrate. Clin. Invest. Med. 121: 271-278, 1988.

Bounous, G. et al: Influence of protein type in nutritionally adequate diets on the development of immunity in "Absorption and utilization of amino acids". C.R.C. Press, Ed. M. Friedman, pp. 219-232, 1989.

Bounous, G. et al: Immunoenhancing property of dietary whey protein in mice: role of glutathione. Clin. Invest. Med. 12: 154-161, 1989.

Papenburg, R. et al: Dietary milk proteins inhibit the development of dimethylhydrazine induced malignancy. In press, Tumor Biology.

Schaedler, R. W., et al: Effect of dietary proteins and amino acids on the susceptibility of mice to bacterial infections. J. Exp. Med. 110: 921-934, 1959.

Hirayama, T.: An epidemiological study on the effect of diet, especially of milk, on the incidence of stomach cancer. Abstr. 9th Int. Cancer Congress, Tokyo, Japan 713, 1966.

Jacquet, J. et al: Nutrition et cancer experimental: cas du lait. C. R. Hebd. Seanc. Acad. de France, 54: 112-120, 1968.

I.A.R.C. International microecology group. Dietary fiber, transit-time, fecal bacteria steroids, and colon cancer in two Scandinavian populations. Lancet II, 207-211, 1977.

OTHER PUBLICATIONS

Gridley, D. S. et al: Modification of Herpes 2-transformed cell-induced tumors in mice fed different sources of protein fat and carbohydrate. Cancer Letters 17: 161–173, 1982.

Nutter, R. L. et al: Modification of a transplantable colon tumor and immune responses in mice fed different sources of protein, fat and carbohydrate. Cancer Letters 18: 49–62, 1983.

Nutter, R. L. et al: BALB/c male mice fed milk or beef protein: Differences in response to 1,2-dimethylhydrazine carcinogenesis. J.N.C.I. 71: 867–874, 1983.

Reddy, G. V., et al: Antitumor activity of yogurt components. J. Food Protection 46: 8–11, 1983.

Tsuru, S. et al: Inhibition of tumor growth by dairy products. J. Clin. Lab. Immunol. 25: 177–183, 1988.

Perdigon, G. et al: Systemic augmentation of the immune response in mice by feeding fermented milks with *Lactobacillus casei* and *Lactobacillus acidophilus*. Immunology 63: 17–23, 1988.

K. R. Marshall, "Industrial Isolation of Milk Proteins: Whey Proteins," *Developments in Dairy Chemistry* (P. F. Fox, ed.), Appl. Sci. Publ., N.Y.:339–373(1982) (Exhibit A).

Rodney J. Brown, "Milk Coagulation and Protein Determination," *Fundamentals of Dairy Chemistry* (N. P. Wong, ed.), Van Nostrand Reynolds Co., N.Y.:5-83–607,(1988) (Exhibit B).

R. McL. Whitney, "Proteins of Milk," *Fundamentals of Dairy Chemistry* (N. P. Wong, ed.), Van Nostrand Reynolds Co., NY: 81–169 (1988) (Exhibit C).

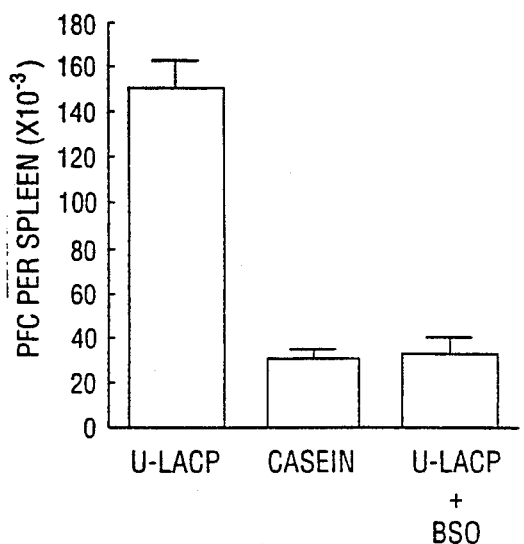
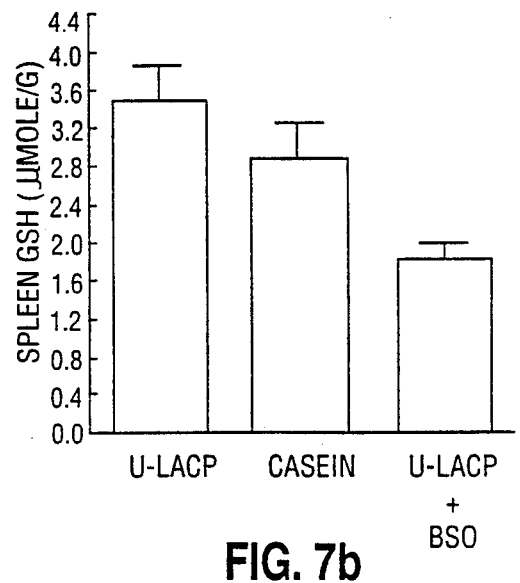

PLAQUE FORMING CELLS ON DAY 5 SHOWING PEAK PRODUCTION OF PLAQUE FORMING CELLS FOLLOWING IMMUNIZATION WITH $10^6$ SRBC.
3 WEEKS DIETARY TREATMENT WITH 20g/100g OF EITHER U-LACP, CASEIN OR U-LACP + BSO

SPLEEN GLUTATHIONE ON DAY 4 SHOWING PEAK LEVELS OF GLUTATHIONE FOLLOWING IMMUNIZATION WITH $5X10^6$ SRBC.
3 WEEKS DIETARY TREATMENT WITH 20g/100g OF EITHER U-LACP, CASEIN OR U-LACP + BSO

BSO = BUTHIONINE SULFOXIMINE

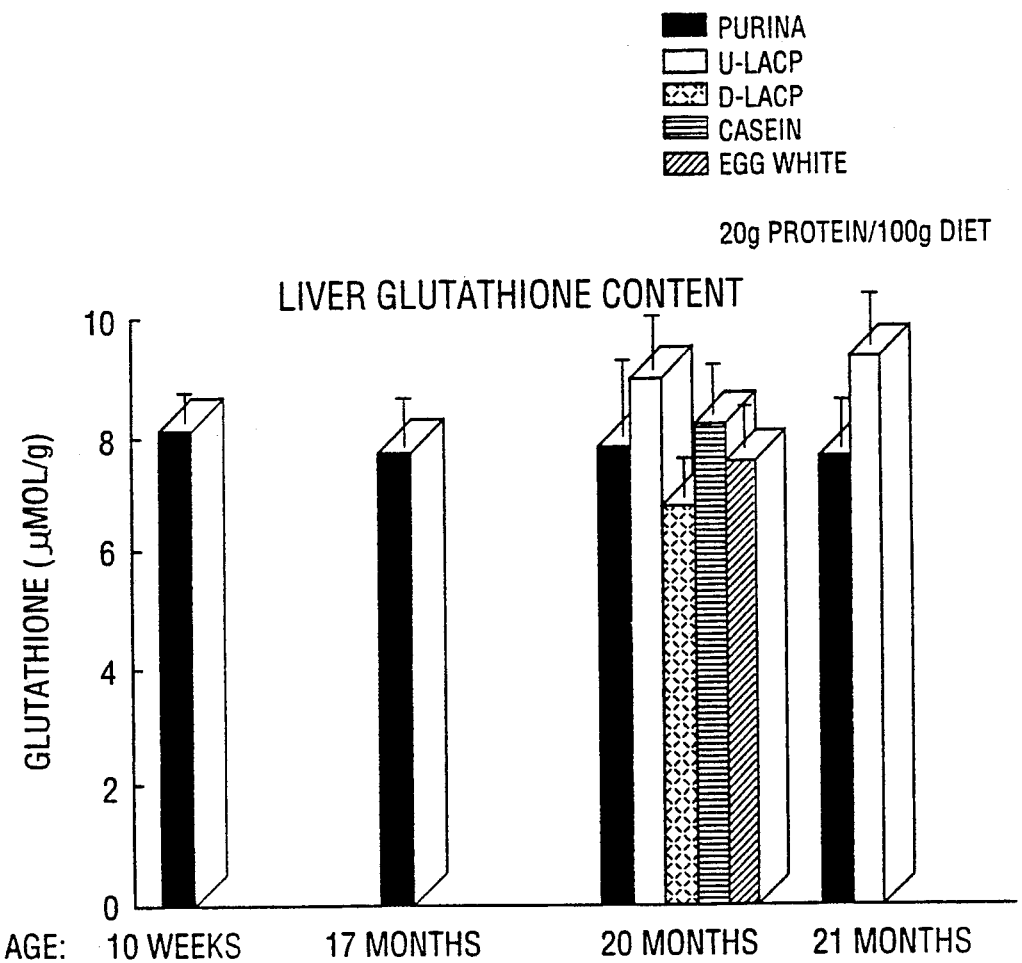
FIG. 8  EFFECT OF DIETARY TREATMENT FROM AGE 17 MONTHS
MALE MICE C57BL/6NIA
MEAN ± STANDARD DEVIATION (n=10)
U-LACP: UNDENATURED WHEY PROTEIN CONCENTRATE
D-LACP: DENATURED WHEY PROTEIN CONCENTRATE
NO INTERGROUP DIFFERENCE IN FOOD CONSUMPTION, BODY WEIGHT AND SERUM PROTEIN.
U-LACP>PURINA, CASEIN, EGG WHITE: $P<0.05$ BY ANOVA (SCHEFFE TEST).
U-LACP>D-LACP: $P<0.01$ BY ANOVA (SCHEFFE TEST).

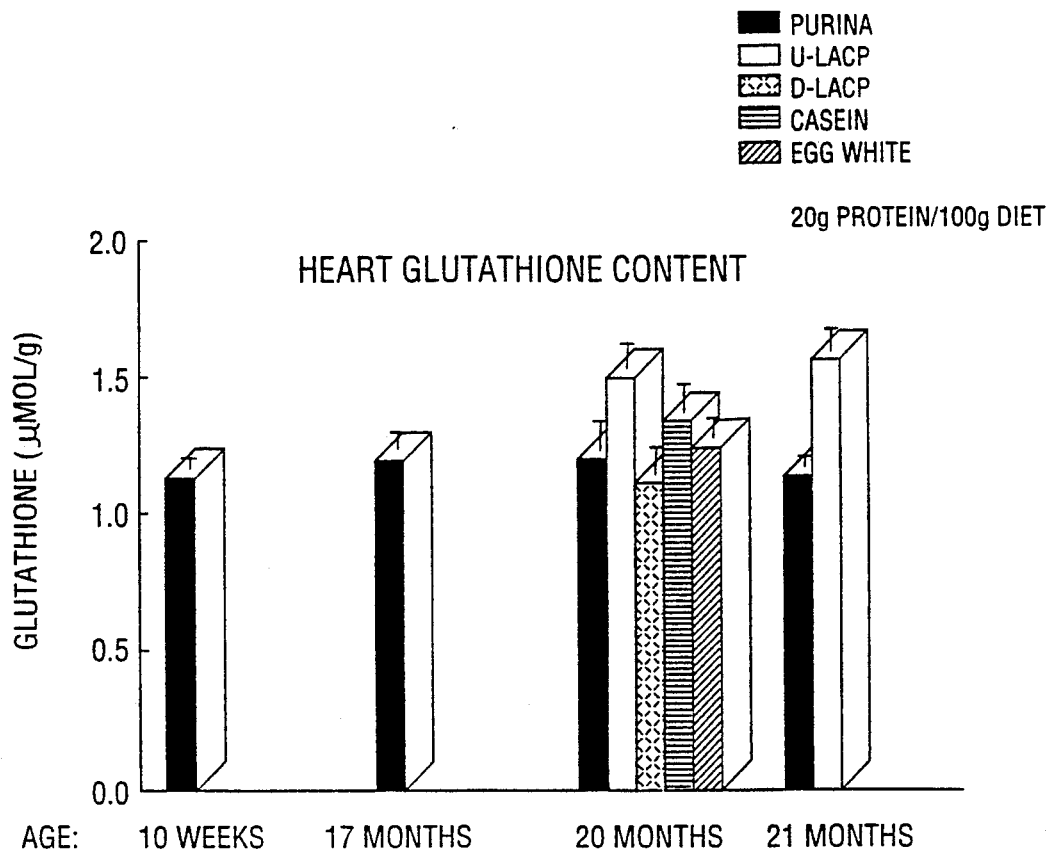
FIG. 9 EFFECT OF DIETARY TREATMENT FROM AGE 17 MONTHS
MALE MICE C57BL/6NIA
MEAN ± STANDARD DEVIATION (n=10)
U-LACP: UNDENATURED WHEY PROTEIN CONCENTRATE
D-LACP: DENATURED WHEY PROTEIN CONCENTRATE
NO INTERGROUP DIFFERENCE IN FOOD CONSUMPTION, BODY WEIGHT AND SERUM PROTEIN.
U-LACP> CASEIN. EGG WHITE: $P<0.05$ BY ANOVA (SCHEFFE TEST).
U-LACP>D-LACP. PURINA: $P< 0.01$ BY ANOVA (SCHEFFE TEST).

21 MONTH OLD MALE C57/BL/6NIA MICE

BIOLOGICALLY ACTIVE WHEY PROTEIN CONCENTRATE

RELATED APPLICATIONS

This application is a continuation-in-part of U.S. application Ser. No. 289,971 filed Dec. 23, 1988, now abandoned, and a continuation of application U.S. application Ser. No. 188,271, filed Apr. 28, 1988, now abandoned.

BACKGROUND OF THE INVENTION

Throughout this application, various publications are referred to by Arabic numerals within parenthesis. Full citations for these references may be found at the end of the specification, immediately preceding the claims. The disclosures of these publications are hereby incorporated by reference in order to more fully describe the state of the art at the time of the invention described and claimed herein.

The present invention is based on the surprising discovery that undenatured whey protein concentrate has an enhanced immunological effect. More specifically, the invention relates to the effect of the oral administration of whey protein concentrate in undenatured conformation on the immune response to sheep red blood cells, host resistance to pneumococcal infections, development of chemically induced colon carcinoma and tissue glutathione.

The present invention shows the correlation between the undenatured conformation of whey protein concentrate (w.p.c.) and host immunoenhancement whereby chemical indices of denaturation are given and the demonstration that the same crucial role of molecular conformation (undenatured state) applies to glutathione GSH promotion, which is the other major biological activity of w.p.c. Equally important is the demonstration that another protein source such as egg white, with the same high cysteine content as w.p.c. does not enhance GSH synthesis, further demonstrating the specificity of w.p.c. with respect to the described biological activity.

Whey and whey protein have been utilized from time immemorable for nutritional purposes. In addition, whey was recommended in folk and ancient medicine for the treatment of various diseases [1,2] and, in one instance, lifetime feeding of hamsters with a whey protein diet has been shown to promote longevity with no explanation given[3,4].

Dairy products are widely used as a good source of nutrition. In addition, claims have been made to the effect that fermented whole milk (yogurt) is beneficial in the management of some types of intestinal infections. Certain dietary regimes based on ill defined natural or cultured dairy products are said to be associated with long life expectancy in some regions of the U.S.S.R., for example, Georgia.

Since time immemorial, serum lactis, which is latin for milk serum or whey, has been administered to the sick for the treatment of numerous ailments. In 1603, Baricelli reported on the therapeutic use of cow or goat milk serum sometimes mixed with honey or herbs. The spectrum of illnesses treated with whey include jaundice, infected lesions of skin, those of the genito-urinary tract with purulent secretions, gonorrhea, epilepsy, quartan fever and other febrile states of different origins. Indeed, the common denominator of most of these illnesses appears to be a septic condition. Although physicians of both ancient times and of the middle ages agreed that whey treatment should be carried out over a period of several days, a difference of opinion appear to exist concerning the daily amount prescribed. Thus, Galen, Hippocrates and Dioscoride insisted on a minimum daily amount of two 12 ounce latin libras, and up to five libras a day according to gastric tolerance. This would represent between one to two liters of whey a day. Baricelli on the other hand, reflecting the trend of his time, limited the amount prescribed to one libra a day, given in fractionated doses on an empty stomach.

Since then, numerous articles published in Europe through the 17th, 18th and 19th centuries have advocated the therapeutic use of whey. In an Italian textbook published in the middle of the 19th century[15], at the dawn of scientific medicine, an interesting distinction is made between whole milk and milk serum. Milk is recommended firstly as a nutrient especially in patients with strictures of the gastro intestinal track. In this respect the author emphasises that the benefits of the then popular "milk therapy" of cachexia and tuberculosis are due only to the nutritional property of milk. Secondly, the milk was prescribed in the treatment of poisoning because milk components would presumably neutralize ingested toxic material. Thirdly, milk therapy was suggested for the alleged capacity of this fluid to coat and soothe ulcers of the gastrointestinal track. Milk serum, on the other hand, was advocated in the treatment of pneumonitis, acute inflammatory diseases of the intestines and urogenital track, in spite of its recognized lower nutritional quality. Finally, the author emphasized the ineffectiveness of whey in the treatment of disorders of the nervous system.

The prime difference between whey (serum lactis) and whole milk is the near absence in the former of the caseins, the casein-bound calcium and phosphate, most of the fat and the fat soluble vitamins. The actual concentration in whey of "whey proteins" is usually similar to that in milk. Hence quantitative differences between whey and milk could not be construed to represent a key factor in the alleged therapeutic effect of whey treatment because, if any, they imply the lack, in whey, of some important nutrients. Some previously collected data [5-10] of the present inventors provide a scientific background to the presumed benefit of intensive treatment with "serum lactis". The importance of the characteristic amino acid and peptide profile of whey protein concentrate in the immune enhancing effect of the whey protein concentrate (WPC) has been shown. The caseins represent 80% of the total protein content of cows milk while WPC is only 20%. Hence, it is conceivable that it is the separation of WPC from the caseins in whey which represents the crucial qualitative change, since this would render the amino acid profile and associated small peptides patterns of whey proteins unaltered by that of the caseins, once the digestive process has released free amino acids from all ingested proteins.

The search for the possible mechanism of immunoenhancement by whey protein feeding has revealed to us the provocative possibility that whey protein concentrate may contribute to a broader biological effect of a protective nature involving susceptibility to cancer and general detoxification of environmental agents. All these conditions appear to be somehow related to changes in glutathione which is a ubiquitous element exerting a protective effect against superoxide radicals and other toxic agents.

Glutathione is a tripeptide thiol (L-gamma-glutamyl-L-cysteinylglycine) with a broad range of vital functions that include detoxification of xenobiotics and protection of cells against oxygen intermediates and free radicals, by-products of oxygen-requiring metabolism[42-45]. Modulation of intracellular glutathione affects the proliferative immune response of lymphocytes which may be inhibited by oxidative injury[46-48]. Glutathione protect the cells against radiation and alkylating agents[49-50]. Age-related or experimentally induced glutathione depletion in the lens is associated with cataract formation[51,52]. Oxidative DNA damage is rapidly and effectively repaired. The human body is continually repairing oxidized DNA. A small fraction of unrepaired lesions, however, could cause permanent changes in DNA and might be a major contributor to old age diseases and cancer[53]. Indeed, several age associated diseases may be induced by free radicals[54]. It appears that whereas data on age-related changes in tissue vitamin E and other antioxidants are, at best, contradictory[55], the tissue glutathione levels are more consistently reported to decline with old age in laboratory animals[56,57] and man[58-61].

For these reasons there has been interest in the factors that influence intracellular glutathione synthesis and especially in ways of increasing cellular levels of glutathione.

Glutathione is composed of three amino acids: glutamic acid, glycine and cysteine. Availability of cysteine is a limiting factor in the synthesis of glutathione[62,63]. Cysteine is derived from dietary protein and by trans-sulfuration from methionine in the liver. Various methods have been tried in order to increase cellular levels of glutathione. Administration of free cysteine is not an ideal method because this amino acid is rapidly oxidized, toxio[64] and may actually cause glutathione depletion[65]. Similar problems have been encountered with i.p. injection of N-acetyl cysteine to rats, although oral administration of this compound appeared to prevent paracetamol-induced glutathione depletion[65]. Administration of compounds that are transported and converted intracellularly into cysteine, such as L-2-oxothiazolidine-4-carboxylate are useful in increasing cellular glutathione[66] acting as an intracellular delivery system for cysteine. Hepatic glutathione doubled four hours after injection, returned to normal 8 hours later but was below normal after 16 hours[66]. Another approach for increasing tissue glutathione levels was found in s.c. injection of gamma glutamylcyst(e)ine in mice: glutathione increased in the kidney by about 55%, 40-60 minutes after injection, returning to near control values 2 hours later[67]. The administered compound is transported intact and serves as a substrate for glutathione synthetase. It was also reported that about 2 hours after i.p. administration of gamma-glutamyl cysteinylglycyl monomethyl (or monoethyl) ester to mice, the liver and kidney glutathione levels were doubled, with return to normal values after 8 hours[68]. Similar increases in glutathione tissue levels were attained by Meister by administering an alkyl monoester of glutathione (U.S. Pat. No. 4,784,685, Nov. 15th, 1988), to mice. Such esters are transported into tissue cells, and are deesterified within the cells, thus leading to increased cellular levels of glutathione. The kinetics of tissue glutathione increments attained with this method are similar to those described following i.p. injection of methyl or ethyl esters of glutathione[68]. The effectiveness of these methods has been clearly demonstrated in acute experiments[68,69]. (U.S. Pat. No. 4,784,685); in mice treated with L-2-oxothiazolidine-4-carboxylate the expected drop in glutathione tissue level subsequent to acetaminophen injection, was replaced by an actual increase in tissue glutathione values and survival. Other methods to increase tissue glutathione levels are based on the "overshoot" of glutathione concentration, following depletion by diethylmaleate or BSO. These studies were done in vitro on murine cell lines[70]. Also pre-exposure of rats to hypoxia was found to increase lung glutathione[71].

The administration of glutathione itself is of little consequence on tissue glutathione levels, because it apparently cannot be transported intact across the cell membrane[68].

Some of said methods of increasing intracellular levels of glutathione concentration are either toxic or dangerous owing to the risks related to the initial phase of glutathione depletion. The methods involving the use of gamma-glutamyloyst(e)ine, athiazolidine or glutathione esters (U.S. Pat. No. 4,784,685) offer an interesting possibility for short term intervention. However, their long term effectiveness in producing sustained elevation of cellular glutathione has not been shown, nor has the possible toxicity of their long term use been disproved. Indeed, glutathione and glutathione disulfide were found to be positive in the most commonly used short term tests for carcinogenicity and mutagenicity. Relevant to our invention are recent data indicating specifically that a lack of the GSH precursor, cysteine, rather than a decrease in biosynthetic enzyme activities is responsible for the deficiency of GSH noted in aging animals[73]. Similarly, the fall in cytosolic GSH in the liver of chronic ethanol fed rats does not appear to be caused by a limitation in the capacity of gamma-glutamylcysteine synthetase activity[74].

Our studies have shown that the observed enhancement of the immune response is associated with greater production of splenic glutathione in immunized mice fed whey protein concentrate in comparison to mice fed casein, cysteine enriched casein or egg white protein in similar dietary concentration. The efficiency of dietary cysteine in inducing supernormal glutathione levels is greater when it is delivered in the whey protein than as free cysteine or within the egg white protein. Glutathione was found at higher levels in the heart and liver of whey protein fed old mice in comparison to mice fed the corresponding casein diet, the egg white protein or Purina Mouse Chow.

The use of mice as biological test subjects in research is commonly practiced world-wide. It is generally accepted that if a biological phenomenon occurs in two different mammalian species, it can be applied to other mammalian species including man. Our studies carried out in several unrelated strains of mice of both sexes therefore are of great benefit in gauging the biological activity of whey protein concentrate which appears to be independent of specific genetic or hormonal influences. Perhaps most importantly human milk has by far the highest whey protein/casein ratio than any other mammal. (See in this regard "Evolutionary Traits in Human Milk Proteins", Bounous et al, Medical Hypotheses (1988) 27, 133-140). Presumably nature has prepared humans, through the only obligatory form of nutrition, to handle undenatured whey proteins for their best metabolic advantage. In fact, one would anticipate that the favourable biological activity of whey protein concentrate in rodents might be more pronounced in the human host.

Definitions (a) Whey Protein:

Whey proteins are the group of milk proteins that remain soluble in "milk serum" or whey after precipitation of caseins at pH 4.6 and 20° C. The major whey proteins in cow's milk are beta-lactoglobulin ($\beta$ L), alpha-lactalbumin ($\alpha$ L), immunoglobulin and serum albumin (SA) in order of decreasing amounts[11].

The product of industrial separation of this protein mixture from whey is called "whey protein concentrate" (WPC) or isolate The WPC used in most of our experiments is from bovine milk (Lacprodan-80 from "Danmark Protein A.S."). Use in its undenatured state is indicated as U- Lacp, and in its denatured state is indicated as D-Lacp. Lactalbumin (L) is the term traditionally used to define WPC.

(b) C=casein;

(c) SRBC=Sheep red blood cells;

(d) PFC=Plaque forming cells (spleen): enumeration of PFC in spleen is used to assess the humoral immune response to SRBC injection;

(e) GSH=Glutathione (L-gamma-glutamyl-L-cysteinylglycine);

(f) DMH=1,2-Dimethylhydrazine.

(g) The defined formula diets tested varied only in the type of protein.

(h) Whey of bovine milk contains approximately 6 g per liter protein, most of the lactose, mineral and water soluble vitamins.

A suitable source of whey protein concentrate is the material known by the trade mark PROMOD, which is a protein supplement provided in powder form by Ross Laboratories, a Division of Abbott Laboratories, U.S.A. This is a concentrated source of high quality protein which is useful for providing extra protein to persons having increased protein needs, or those who are unable to meet their protein needs with their normal diet. It contains whey protein concentrate and soy lecithin. It has the following nutrients:

| NUTRIENTS | PER 5 G PROTEIN (ONE SCOOP) |
|---|---|
| Protein | 5.0 g |
| Fat | Does not exceed 0.60 g |
| Carbohydrate | Does not exceed 0.67 g |
| Water | Does not exceed 0.60 g |
| Calcium | Does not exceed 23 mg (1.15 mEq) |
| Sodium | Does not exceed 13 mg (0.57 mEq) |
| Potassium | Does not exceed 65 mg (1.66 mEq) |
| Phosphorus | Does not exceed 22 mg |
| Calories | 28 |

It has the following typical amino acid composition per 100 g protein. 100 g PROMOD protein yields approximately 105 g of amino acids.

TYPICAL AMINO ACID COMPOSITION per 100 g Protein

Essential Amino Acids:
Histidine, 1.9 g;
Isoleucine, 6.2 g;
Leucine, 10.8 g;
Lysine, 9.3 g;
Methionine, 2.2 g;
Phenylalanine, 3.6 g;
Threonine, 7.3 g;
Tryptophan, 1.9 g;
Valine, 6.0 g.

Non-Essential Amino Acids:
Alanine, 5.3 g;
Arginine, 2.6 g;
Aspartic Acid, 11.2 g;
Cysteine, 2.6 g;
Glutamic Acid, 18.2 g;
Glycine, 2.1 g;
Proline, 6.5 g;
Serine, 5.6 g;
Tyrosine, 3.4 g

Diets used in our studies

Diets are prepared in the following way: 20 g of selected pure protein, 56 g of product 80056 protein free diet powder containing corn syrup, corn oil, tapioca starch, vitamins and minerals (Mead-Johnson Co. Inc., U.S.A.), 18 g cornstarch, 2 g wheat bran; 0.05 g Nutramigen vit-iron premix (Bristol-Myers, Ontario, Canada), 2.65 g KCl; 0.84 g NaCl. The carbohydrate and lipid components of our formula diets were the same. The only variable in the various purified diets was the type of protein (20 g protein/100 g diet). At this concentration in diet all the different proteins tested provided the daily requirements of essential amino acids for the growing mouse[12]. Vitamins and minerals were the same in each set of experiments and were added in the amount necessary to provide daily requirements for the growing mouse[13,14]. Table 1, below, indicates the variation in suggested vitamin requirements for mouse diets and their contents in some of our formulations. Therefore all the formula diets used in our experiments were designed to provide adequate nutrition as demonstrated by normal body growth, serum protein and by the absence of hair loss, dermatitis, cataract, ataxia, fatty liver etc. The latter symptoms were of course present in very old mice and were related to the aging process.

TABLE 1

| VITAMIN AND MINERAL CONTENT OF TEST DIETS (amount/100 g diet) | | | | |
|---|---|---|---|---|
| | TEST DIETS | | JACKSON (1) (range of amount recommended in Jackson laboratories diets) | |
| VITAMINS: | | | | AIN 76 (2) |
| Vitamin A, IU | 1295 | 1800 | 24–550 | 400 |
| Vitamin D, IU | 260 | 360 | 14–506 | 100 |

TABLE 1-continued
VITAMIN AND MINERAL CONTENT OF TEST DIETS (amount/100 g diet)

| | TEST DIETS | | JACKSON (1) (range of amount recommended in Jackson laboratories diets) | |
|---|---|---|---|---|
| Vitamin E, IU | 11.6 | 18 | 1–2.7 | 5.0 |
| Vitamin K, mg | 0.06 | 0.09 | — | 0.005 |
| Thiamine(Vitamin B1), mg | 0.34 | 0.63 | 0.22–0.99 | 0.60 |
| Riboflavin(Vitamin B2), mg | 0.38 | 0.69 | 0.24–1.1 | 0.60 |
| Vitamin B6, mg | 0.26 | 0.36 | 0.1–0.55 | 0.70 |
| Vitamin B12, mg | 0.0012 | 0.054 | 0.0039–0.0055 | 0.001 |
| Niacin, mg | 5.1 | 9.2 | 2.6–14.3 | 3.0 |
| Folic acid, mg | 0.063 | 0.12 | .05–.27 | 0.2 |
| Pantothenic acid, mg | 1.93 | 3.38 | 1–5.5 | 1.6 |
| Biotin, mg | 0.031 | 0.058 | 0.019–0.165 | 0.02 |
| Vitamin C, mg | 53.3 | 65 | — | — |
| Choline, mg | 44 | 76 | 49–145 | 100 |
| Inositol, mg | 19.8 | 19.8 | — | — |
| MINERALS: | | | | AIN 76 |
| Calcium, mg | 430 # | | | 520 |
| Phosphorus, mg | 260 # | | | 400 |
| Magnesium, mg | 63.2 # | | | 50 |
| Iron, mg | 7.9 | | | 3.5 |
| Zinc, mg | 3.57 # | | | 3.0 |
| Copper, mg | 0.47 # | | | 0.60 |
| Iodine, mg | 0.023 | | | 0.02 |
| Sodium, mg | 232 | | | 100 |
| Potassium, mg | 997 | | | 360 | after minerals analysis
(1) Hoag W. G., Dickie M. M. "Nutrition: in Green E. L. (Ed) Biology of the laboratory mouse McGraw-Hill NY 1966 pp 39–43. Jackson was our supplier.
(2) The mouse in biomedical research, vol III Eds Foster H. L., Seall J. D., Fox J. B., Academic press 1983, NY pp 57–58

Immunization for Plaque Assays

The diet-fed mice were immunized by an intravenous injection of $5 \times 10^6$ washed sheep red blood cells obtained weekly from Institut Armand-Frappier, Laval des Rapides, Quebec, Canada.

Plaque Forming Cell (PFC) Assay

The method used for assaying IgM plaque forming cells was essentially the one described by Cunningham and Szenberg[101], with certain minor modifications. Spleen cell suspensions were prepared by gently tamping the spleen through a 50-mesh stainless steel screen, and collecting the cells in balanced salt solution (BSS) supplemented with 10% heat-inactivated calf serum (Grand Island Biological Company, Montreal, Quebec, Canada). The spleen cells were washed and made up to 15 ml with BSS. Sheep red blood cells were washed twice and made up to a 20% concentration. Guinea pig serum (Grand Island Biological Company, Montreal, Quebec, Canada) as a source of complement was diluted 1/15 with BSS All stock solutions were kept on ice water until used The test consisted of mixing 0.05 ml of spleen cells, 0.15 ml of sheep red blood cells and 0.75 ml of the complement solution in a test tube at 37° C. The whole mixture was immediately withdrawn and put into slide chambers, sealed with warm paraffin wax, and incubated at 37° C. for 45 to 60 min. The number of plaque forming cells was counted and their total number per spleen estimated by multiplying the number of plaque forming cells in each sample (0.05 ml spleen cells) by 300. The values are expressed per total organ rather than per $10^6$ spleen cells, since this appears to reflect more accurately the functional status of the spleen per se.

Mice were assayed for the plaque forming cell response to sheep red blood cells normally on the fifth day after immunization when the response was shown to peak or, in the kinetic study, on days 3, 4, 5 and 6 post-immunization.

Statistics

The mean plaque forming cell values were compared among the dietary groups using either Student's test, when two groups were being compared, or the of variances (ANOVA) for more than two groups. Because of the heterogeneity of variances among groups, the adjustment given by Brown and Forsythe was used

Spleen Glutathione Content

Ninety milligrams of mouse spleen were weighed using a Mettler PM-300 balance and samples varied from 90 mg by less than 5 mg (5%). The samples were then homogenized in 5-sulfosalicylic acid (5% w/v) Homogenates were centrifuged for 5 min in a microfuge at $10,000 \times g$. The assay was carried out using the supernatants on the same day according to the methods of Anderson[72]. Values are expressed as $\mu$mol per g/wet tissue.

Buthionine Sulfoximine Experiments

In some experiments, following three weeks of whey protein feeding and one day prior to immunization with sheep red blood cells, mice were injected i.p. with 450 mg/kg of buthionine sulfoximine (BSO) (S-[n-butyl] homocysteine sulfoximine), a specific inhibitor of gamma-glutamyloysteine synthetase At the same time 20 mM of BSO was added to the drinking water

Description of the Prior Art

An imposing number of publications deal with the association of nutritional deficiencies, including protein energy malnutrition, and infection in the human and animal host[16]. For example, mice fed with insufficient amounts of protein, exhibit less growth or even weight loss and increase the susceptibility to infection by *Staphylococcus aureus*[17].

French Patent Publication 2,296,428 relates to the dietetic and therapeutic use of lactoserum protein compositions for the treatment for the treatment of malnutrition and diarrhea of, diarrhea, in infants and adults. This reference, however, does not establish the biological activity (immunoenhancement) of the whey protein diet unrelated to its nutritional quality. The improvement shown by the subjects treated with these whey protein compositions appeared to result from the increased nourishment from the protein compositions particularly in studies relating to malnourished infants.

British Patent Specification 1,495,940 relates to an anti-cancer active whey fraction. A whey fraction having the molecular weight of from 6000 to 20,000 is utilized (I.P. injection) in the treatment of cancer and leukemia. The particular mechanism of the effective fractions of whey against cancer has not been shown. This includes irradiated whey.

PCT/U.S 87/00036 (WO87/04050) relates to an immunologically active whey fraction and recovery process. Disease resistance and growth rates in animals including humans is enhanced by oral administration of the whey fraction. This reference discloses a method for concentrating from whey, a product containing immunologically active (antigen binding) immunoglobulin [Ig]]that, when fed to new born calves at a very high concentration of 7% of total solids, provides a substantial transfer of natural passive immunity as evidence by blood Ig levels and increased resistance to infections. This reference does not appreciate nor prove a cause-effect relationship between passive immunity and the development of active immunity.

Dietary protein deficiency has been found to reduce the incidence of spontaneous[80] or transplanted[80,81] tumors. Most of the definitive studies concerning protein and cancer have utilized protein underfeeding. Although some evidence indicates that the higher the protein intake, the greater the tumor incidence[82,83], data concerning the effect of raising protein intake on carcinogenesis and tumor development are not definitive[84]. Studies have focused on the quantity of protein and its amino acid supply rather than its source[84]. Only a few data are available on the effect of protein type in nutritionally adequate and similar diets on the development of tumors.

Jacquet et al[85] reported that feeding milk retarded on the average by a factor of 0.4 tumor growth in rats implanted with epithelioma T8. This is consistent with some epidemiological studies showing that consumption of milk or dairy products may reduce the risk of cancer[86,87]. In mice inoculated with Ehrlich ascites tumor cells, feeding yogurt reduced the number of tumor cells by a factor of 0.2–0.28[88]. It was also reported that mice fed a milk protein formula diet, exhibited inhibition of tumor volume by a factor of 0.2 to 0.7, following s.c. injection of DMH-induced colon tumor cells in comparison to mice fed other types of protein[89]. A comparable degree of tumor inhibition was noted in milk protein fed mice injected s.c. with herpes virus transformed cells[90]. However, in another article, submitted several months later, the same group of authors reported results "... different from those expected in light of our previous findings". Milk protein feeding did not inhibit tumor growth in the same strain of mice injected with DMH[91]. The previously reported anti-cancer biological property of dietary milk proteins was absent, in spite of the preservation of their good nutritional quality[91]. The authors provide no explanation for the apparent contradiction.

DMH-induced colon tumors appear to be similar to those found in humans as far as type of lesions and chemotherapeutic response characteristics are concerned[93,94].

In light of our findings on the lability cf the biological property of whey protein concentrate, it is conceivable that the whey protein fraction of the milk protein mixture, used in the later experiments, was partially or totally denatured. Various types of cheeses and yogurt were recently found to suppress the growth of several experimental tumors in mice in proportion to the duration of feeding. The tumor size was reduced by a factor of 0.17 to 0.70 depending on the type of tumor[92]. In spite of variations in the type of tumor and in the control diets used in all these studies it is apparent that the level of tumor inhibition reported with dairy product feeding is comparable to that which we obtained with a formula diet containing casein as protein source.

These previous uses of whey protein in various forms and the treatment of various diseases do not appreciate the enhancement of the immunological effect of the whey protein concentrate when in undenatured conformation and in many cases improvement of the patient is a result of the nutritional benefit of whey. Further, this biological activity is dependent on the combined effect of all the protein components of the whey protein concentrate and cannot be obtained using whey protein fractions. Should a presumed biologically active material form a part of a particular protein component, it is apparent that its effective bioavailability is strongly influenced by the co-existence of the other protein components of WPC through digestive-absorptive process. The activity is not specifically related to the nutritional efficiency of the whey protein concentrate. Denaturation abolishes the described biological activity without affecting the nutritional quality of the whey protein concentrate.

Accordingly, the principle object of the present invention is to provide a method for improving the humoral immune response in mammals by the oral administration of undenatured whey protein concentrate.

A further object of the invention is to provide a method for increasing the concentration level of glutathione in the organs of mammals through the use of undenatured whey protein concentrate through its oral administration.

A further object of the invention is a process for enhancing the resistance to bacterial infection, particularly pneumococcal infection, enhanced resistance to slow growing carcinoma such as colon carcinoma through the utilization of whey protein concentrate in an undenatured state.

SUMMARY OF THE INVENTION

The present invention relates to a biologically active whey protein composition comprising a suitable concentration of whey protein concentrate wherein the whey protein concentrate contains the proteins which are present in an undenatured state and wherein the biological activity of the undenatured whey protein concentrate is based on the overall amino acid and associated small peptides patterns resulting from the contribution of all its protein components.

The invention further relates to the inclusion of Vitamin $B_1$ and $B_2$ in the biologically active whey protein at above the minimum recommended daily requirements resulting in a composition having a further increase in biological activity.

The invention still further relates to a method for producing a whey protein concentrate composition comprising the steps of: a) immediately after milking, cooling the milk to a temperature in the range of 2° C. to 10° C. and removing impurities, b) after another cleaning of the milk, precipitation of the curd by reducing the pH to about 4.6 with lactic acid initially at 20° C. c) addition of rennet and raising the temperature to about 30° C. for 20 minutes to promote expulsion of whey from the curd and followed by agitation to resolve at low speed, d) thermal treatment of the pasteurization type of the remaining product in the vat and agitation at high speed for cheese production, e) irradiation and separation of the whey, and f) ultrafiltration of whey using a membrane having a molecular weight cut off of substantially 10,000 or less, said method being characterized in that the fraction of whey to be used for subsequent production of whey protein concentrate is not heated and the material from which it is derived is slowly agitated to minimize protein denaturation, said ultrafiltration being carried out in a production line comprising up to 20 frame-type modules holding a large number of membranes achieving a final undenatured protein concentrate in dry matter, wherein said ultrafiltration is carried out at a temperature in the range of 4° C. to 20° C.

The invention still further relates to a method for improving the humoral immune response in mammals, the method comprising the steps of administering orally to a mammal, a therapeutically or prophylactically effective amount of undenatured whey protein concentrate having biological activity wherein the biological activity is based on the overall amino acid and associated small peptides pattern resulting from the contribution of all its protein components. Enhancement of the humoral immune response results in enhanced resistance to bacterial infection, particularly pneumococcal infection; enhance resistance to colon carcinoma, particularly chemically induced colon carcinoma; delayed or decreased mortality or a combination of the above.

The invention yet further relates to increasing the rate of synthesis, rate of replenishment and concentration levels of glutathione in animal organs through the step of administering to an animal a therapeutically or a prophylactically effective amount of undenatured whey protein concentrate having biological activity, the biological activity being based on the overall amino acid and associated small peptides pattern resulting from the contribution of all its protein components.

The invention also relates to various food supplements, drugs and the like containing the biologically active whey protein composition alone or in combination with Vitamins $B_1$ and $B_2$.

The above, and other objects, features and advantages of the present invention, will become apparent from the following detailed description of preferred embodiments to be read in conjunction with the accompanying drawings.

BRIEF DESCRIPTION OF THE DRAWINGS

In the drawings which form part of this specification:

FIG. 7a illustrates plaque forming cells/spleen (PFC) on day 5, and FIG. 7b shows spleen glutathione levels on day 4, following immunization with $10^6$ sheep red blood cells (SRBC).

FIG. 8 illustrates the liver glutathione content in male mice C57BL/6NIA fed undenatured whey protein (U-Lacp), denatured whey protein (D-Lacp), casein, egg white protein or purina diet-fed counterparts at age 10 weeks, 17, 20 and 21 months.

FIG. 9 illustrates the heart glutathione content of male mice C57BL/6NIA fed undenatured whey protein (U-Lacp), denatured whey protein (D-Lacp), casein, egg white protein or purina diet-fed counterparts at age 10 weeks, 17, 20 and 21 months.

DETAILED DESCRIPTION OF THE INVENTION

An assessment has been made of the effect on the immune response Of different types of proteins in nutritionally adequate and similar diets. Mice fed formula diets containing 20% or 28% whey protein pancreatic hydrolysate (LAD, Nestle) were found to produce more plaque forming cells to sheep red blood cells than mice fed Purina mouse chow containing about 22% protein from various sources and of similar nutritional efficiency. The immunoenhancing effect of LAD was maximal at 20% concentration[5]. A 20 g net protein/100 g diet provides a good method to assess the effect of protein type on the immune system. At this level most protein supplies the minimum daily requirement of all indispensible amino acids for the growing mouse[12-14] and this is important because the amino acid adequacy is not the variable under investigation.

In subsequent studies, a comparison was made regarding the effect of dietary whey protein concentrate (WPC) to that of other purified proteins in formula diets of similar nutritional efficiency. The effect of graded amounts of dietary WPC, casein (C), soy (S), wheat (W), protein and Purina rodent chow (stock diet) on the immune responsiveness of C3H/HeN mice has been investigated by measuring the specific humoral immune response to sheep red blood cells (SRBC), and horse red blood cells (HRBC). The nutritional efficiency of these diets was normal and similar. The immune response of mice fed the WPC diets, was found to be almost five times higher than that of mice fed the corresponding C diets. The humoral immune response of mice fed C, S, and W diets was substantially lower than that of mice fed stock diet, whereas that of mice fed L (WPC) diet was higher. The above-described immune effect of all tested proteins was obtained at 20 g/100 g concentration with no further increments with 30- and 40 g/100 g protein in the diet[7].

Because the whey protein concentrate was tested in comparison to a limited number of proteins, we could not ascertain at that time whether the enhancement of the humoral immune response observed in five (5) unrelated strains of mice fed a whey protein diet, was due to a real immunoenhancement, in absolute terms, by whey protein feeding or immuno-depression by the other food proteins tested.

Indeed, it can now be stated that these few purified food proteins (casein, soy and wheat) used as "control" for the whey protein mixture were immunosuppressive when compared to all of the other purified food proteins subsequently tested, though nutritionally adequate and similar at 20% concentration in diet.

Figure 1:
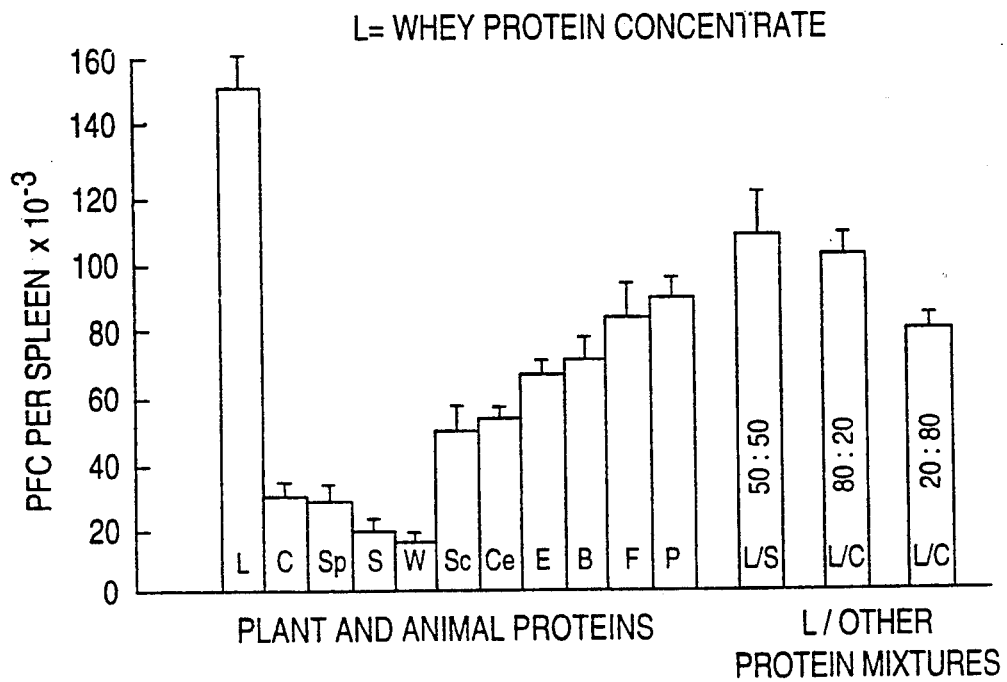
FIG. 1 shows plaque forming cells/spleen (PFC) on the day showing peak production of PFC following immunization with $10^6$ SRBC. Effect of two weeks of dietary treatment with 20 g/100 g diet of either lactalbumin (L) i.e. whey protein concentrate, casein (C), *Spirulina maxima* protein (Sp), soy protein (S), wheat protein (W), Scenedesmus protein (So), corn (Co) protein, egg white protein (E), beef protein (B), fish protein (F), Purina Mouse Chow (P), or 20 g/100 g diet of a mixture containing 50% L and 50% S (L/S), or 80% L and 20% C, or 20% L and 80% C (L/C). Each value represents the mean±SD.

In fact, subsequent testing of whey protein against most commercially available purified food proteins (casein, soy, wheat, corn, egg white, beef, fish protein, gamma globulin, beta-lactoglobulin, alpha-lactalbumin, serum albumin, *spirulina maxima* or *scenedesmus algae* protein) established that indeed mice fed whey protein concentrate exhibit the highest immune response to foreign antigen (SRBC)[31] (FIG. 1). These proteins are nutritionally similar and adequate at the 20 g/100 g diet concentration (Table 2, below).

As indicated in FIG. 1, mice fed the lactalbumin (w.p.c.) diet for 2 weeks exhibit a plaque forming cell response to sheep red blood cells which is higher than that of mice fed any other protein type or Purina mouse chow. The mean number of plaque forming cells per spleen 5 days after i.v. injection with $5 \times 10^6$ sheep red blood cells; in the lactalbumin diet-fed mice was 487%, 494%, 736%, 927%, 309%, 284%, 230%, 214%, and 177% of that noted in casein, Spirulina, soy protein, wheat protein, Scenedesmus, corn protein, egg albumin, beef or fish protein diet-fed mice respectively, and 168% of that of Purina-fed mice. These differences are all statistically significant (P=0.004). The number of plaque forming cells per spleen in Purina-fed mice was 170% of that in corn protein diet-fed mice (P=0.0005) and the value of the latter group was 171% of that noted in casein-fed mice (P=0.0005). No significant difference was observed between fish protein diet-fed, beef protein diet-fed and Purina-fed groups.

The addition of lactalbumin (w.p.c.) to either soy protein or casein produced a significant increment in the humoral immune response of the host. In a 50:50 mixture with soy protein, lactalbumin induced a 4-fold increment in the immune response in comparison to a purely soy protein diet. In an 80:20 mixture with casein, lactalbumin induced a 3-fold increment and, in a 20:80 mixture with this protein, a 2-fold increase in the immune response was seen in comparison to a purely casein diet. It was found that mice fed a lactalbumin diet for at least 2 weeks exhibit a sustained enhancement of the humoral immune response to sheep red blood cells in comparison to mice fed most of the commercially available edible animal or plant proteins in formula diets of comparable nutritional efficiency. This effect persists as long as dietary treatment is continued (up to 2 months has been tested). It is clear that despite great differences in immune response to SRBC, no difference is seen in food consumption, final weight, and serum proteins among mice fed the various purified proteins at 20 g/100 g diet concentration (see Table 2, below).

Thus, it can now be concluded that the newly discovered immune enhancing biological activity of whey protein concentrate is not related to the already known nutritional quality of this protein which is primarily based on digestibility and amino acid content. In fact, the nutritional property of whey protein concentrate at 20 g protein per 100 g diet concentration as used in experimentation is similar to that of the other proteins tested.

TABLE 2

| | Effect of 19 days dietary regimen on food consumption, body growth, total serum protein and edevelopment of spleen[h] | | | | | |
|---|---|---|---|---|---|---|
| Protein type | Avg Consumption (g/mouse/day ± SEM)[a] | Initial Weight (g)[b] | Final Weight (% initial wt.)[c] | Serum Protein (g/100 ml)[d] | Average Spleen | |
| | | | | | Wt. (mg)[g] | cells $10^6$ ± SEM[f] |
| Lactalbumin[j] | 2.8 ± 0.1 | 22.6 ± 0.6 | 118.0 ± 3.2 | 5.8 ± 0.2 | 117 ± 2.1 | 194 ± 4.0 |
| Casein | 2.9 ± 0.2 | 23.0 ± 0.8 | 117.8 ± 4.6 | 6.1 ± 0.3 | 113 ± 3.6 | 150 ± 4.1 |
| Spirulina maxima protein | 2.9 ± 0.3 | 19.8 ± 0.9 | 121.0 ± 1.8 | 5.4 ± 0.5 | 104 ± 3.4 | 138 ± 6.0 |
| Soy protein | 3.1 ± 0.2 | 21.2 ± 0.3 | 114.1 ± 1.3 | 6.0 ± 0.4 | 107 ± 3.8 | 144 ± 4.3 |
| Wheat protein | 2.9 ± 0.2 | 20.0 ± 0.3 | 115.0 ± 2.2 | 5.9 ± 0.3 | 109 ± 2.6 | 139 ± 8.0 |
| Scenedesmus protein | 3.1 ± 0.4 | 23.0 ± 0.3 | 113.0 ± 3.0 | 6.1 ± 0.1 | 107 ± 4.0 | 152 ± 10.0 |
| Corn protein | 3.1 ± 0.2 | 22.8 ± 1.1 | 115.5 ± 5.4 | 5.6 ± 0.2 | 118 ± 3.2 | 160 ± 2.0 |
| Egg albumin | 3.0 ± 0.1 | 20.7 ± 0.6 | 116.0 ± 2.9 | 5.8 ± 0.3 | 114 ± 3.0 | 157 ± 6.0 |
| Fish protein | 2.8 ± 0.4 | 20.9 ± 0.3 | 117.1 ± 1.3 | 5.5 ± 0.1 | 105 ± 2.4 | 152 ± 5.0 |
| Beef protein | 2.9 ± 0.4 | 22.0 ± 0.3 | 113.0 ± 1.9 | 5.7 ± 0.3 | 109 ± 1.8 | 150 ± 5.0 |
| Lactalbumin/Soy (50:50) | 2.9 ± 0.3 | 20.7 ± 0.5 | 121.0 ± 4.7 | 5.8 ± 0.5 | 110 ± 8.0 | 180 ± 7.0 |
| Lactalbumin/Casein (80:20) | 2.7 ± 0.4 | 23.6 ± 0.4 | 121.0 ± 2.0 | 5.6 ± 0.4 | 112 ± 4.0 | 148 ± 4.9 |
| Lactalbumin/Casein | 3.0 ± 0.2 | 23.4 ± 0.5 | 116.0 ± 2.0 | 6.0 ± 0.3 | 118 ± 4.0 | 145 ± 5.0 |

TABLE 2-continued

Effect of 19 days dietary regimen on food consumption, body growth, total serum protein and edevelopment of spleen[h]

| Protein type | Avg Consumption (g/mouse/day ± SEM)[a] | Initial Weight (g)[b] | Final Weight (% initial wt.)[c] | Serum Protein (g/100 ml)[d] | Average Spleen Wt. (mg)[3] | cells $10^6$ ± SEM[f] |
|---|---|---|---|---|---|---|
| (20:80) Nonpurified diet[g] | 3.2 ± 0.3 | 21.1 ± 0.5 | 114.7 ± 1.8 | 5.8 ± 0.2 | 114 ± 1.9 | 189 ± 6.0 |

[a]The average food consumption over the 18 days feeding period was not considered different by ANOVA
[b,c,d,e]The average initial body weight (b), increase in body weight (c), total serum protein (d) and spleen weight (e) were not considered different by ANOVA. The numbers of cells per spleen (f) in lactalbumin and Purina fed groups were higher by ANOVA (p: 0.0001) than the corresponding values in the casein, wheat, soy and fish protein groups.
[g]Purina mouse chow, Ralston Purina Company, St. Louis, MO., (estimated 22 g protein from various sources per 100 g diet).
[h]Mice received $5 \times 10^6$ SRBC on day 14.
[j]Lactalbumin = Whey Protein Concentrate.

Figure 2:
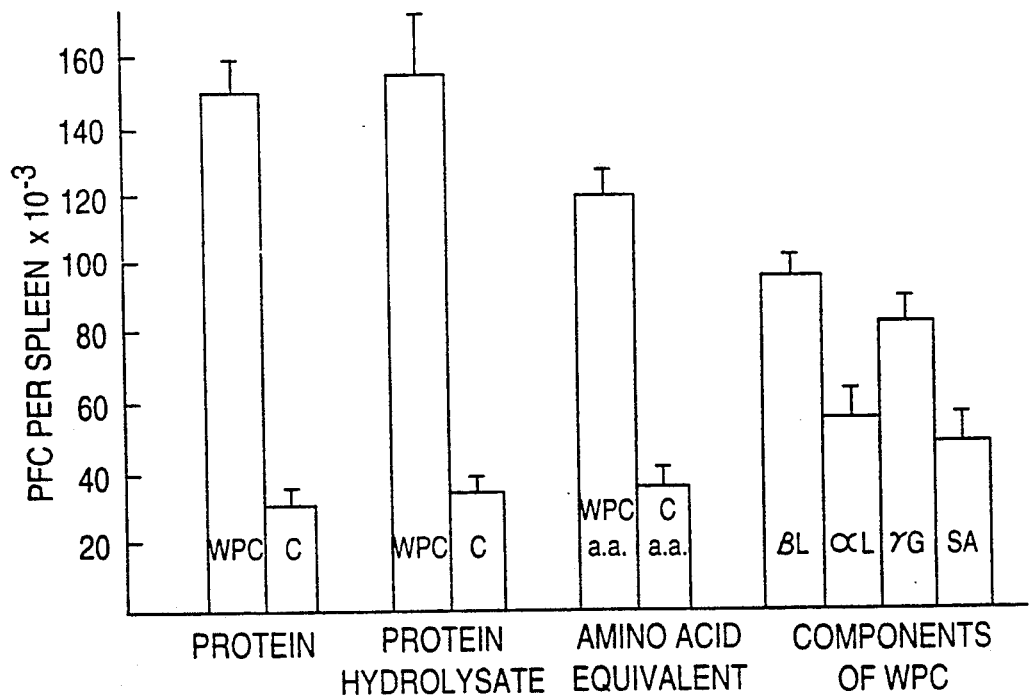
FIG. 2 shows plaque forming cells/spleen (PFC) on the day showing peak production of PFC following immunization with $10^6$ SRBC. Effect of 3 weeks of dietary treatment with 20 g/100 g diet of either whey protein concentrate (WPC), casein (C), whey protein concentrate hydrolysate, casein hydrolysate, beta-lactoglobulin ($\beta$L), alpha-lactalbumin ($\alpha$ L), gamma-globulin ($\gamma$ G) or bovine serum albumin (SA). Each value represents the mean±SD.

FIG. 2 shows plaque forming cells/spleen (PFC) on the day showing peak production of PFC following immunization with $10^6$ SRBC. Effect of 3 weeks of dietary treatment with 20 g/100 g diet of either whey protein concentrate (WPC), casein (C), whey protein concentrate hydrolysate, casein hydrolysate, beta-lactoglobulin ($\beta$ L), alpha-lactalbumin ($\alpha$ L), gamma-globulin ($\gamma$ G) or bovine serum albumin (SA). Each value represents the Means±SD When protein hydrolysate was given, the plaque forming cell response in mice fed the whey protein diet was found to be 504% of that noted in the casein diet-fed mice (p=0.0004) (FIG. 2). When free amino acid mixture was given, the plaque forming cell response in mice fed the whey protein amino acid diet was found to be 332% of that of the casein amino acid diet-fed counterpart (p=0.0001) (FIG. 2). Our results (FIG. 2) indicate that animals fed diets containing 20 g/100 g diet of any one of the four major components of whey protein ($\beta$ L, $\alpha$ L, $\gamma$ G, SA) developed a plaque forming cell response to sheep red blood cells inferior to (p±0.0002) that of mice fed a diet containing 20 g whey protein/100 g diet.

PREPARATION OF UNDENATURED WHEY PROTEIN CONCENTRATE

Immediately after milking, the milk is cooled to 4° C. and kept in a cooling tank for delivery to the cheese factory. The precipitation of the curd is obtained by reducing the pH to about 4.6 with lactic acid initially at 20° C. Following the addition of rennet (normally three ounces/1000 pounds of milk), the temperature is raised to about 30° C. for 20 minutes to promote expulsion of whey from the curd, allowing the agitation in the vat to resolve at low speed.

When sufficient quantity of whey is obtained, the product remaining in the vat is pasteurized in the standard fashion to obtain reduction of bacteria and agitated at high speed for cheese production. The whey is then irradiated with a source of gamma-irradiation. The radiation dose will vary from 5 to 15 kGy according to bacteria content of the whey, to reach equivalent antibacterial effect of standard pasteurization with minimal protein denaturation (measured by changes in soluble protein, i.e. protein concentration in whey before and after treatment).

To obtain primarily undenatured whey to be used for subsequent production of whey protein concentrate, the whey is not heated and the material from which it is derived is slowly agitated to minimize protein denaturation. The prevention of denaturation by maintaining high solubility avoids co-precipitation of whey proteins with the caseins, whey protein loss is minimized, thus increasing the protein content of whey. The whey is then cooled to 6° C.

For the production of undenatured whey protein concentrate, the whey is separated and concentrated through ultrafiltration, which allows for selective separation of protein from lactose, salts and water under mild conditions of temperature and pH. This is a physicochemical separation technique in which a pressurized solution flows over a porous membrane. The membrane allows the passage of only relatively small molecules.

To prevent excessive microbial growth during residence time and protein denaturation, the plant is operated below 10° C. most of the time. A thin layer membrane of polymeric material (polysulphone) with a cut off value of approximately 10,000 is used, so that protein components of MW≧15,000 and more are retained To speed up filtration, the liquid is fed on the membrane at a pressure of 5 bar ($Kg/cm^2$).

A frame type module is constructed to hold a large number of these membranes. The production line consists of 18 such modules. In the last 10 modules, demineralized water is added and then removed through the membranes carrying lactose and minerals with it. To maintain velocities adequate to minimize concentration polarization and fouling, recirculation pumps are used in each stage.

A final protein concentrate with 80% protein (undenatured) in dry matter can be thus achieved.

FACTORS RESPONSIBLE FOR THE IMMUNOENHANCING EFFECT OF WHEY PROTEIN CONCENTRATE IN DIET

(a) Whey Protein Mixture

Our studies show that the immunoenhancing effect of WPC in comparison to C is maintained when these two proteins are replaced in formula diets by a pancreatic hydrolysate (20% free amino and 80% oligo peptides with MW less than 1000) (see FIG. 2)[(32)]. Our results also indicate that mice fed diets containing any one of the four major protein components of the WPC mixture developed a PFC response to SRBC inferior to that of mice fed the corresponding whey protein mixture. We can thus conclude that the observed immunoenhancing effect of WPC is dependent upon the contribution of all its protein components. For these reasons we can assume that this phenomenon is not related to milk protein allergy or some other manifestation of oral immunization.

(b) Undenatured Conformation of the Whey Protein Concentrate

Recent observations have revealed to us that the described biological activity of the whey protein concentrate, already shown to be unrelated to its nutritional quality, is actually dependent on the undenatured conformation of the proteins. This discovery was made accidentally when a batch of whey protein concentrate that was sent to us by the usual supplier failed to exhibit the immunoenhancing effect previously described while exhibiting the same nutritional efficiency. Upon analysis it appeared that this preparation was less soluble and exhibited all the characteristic indirect signs of denaturation (D-Lacp), quite different indeed from the previous samples of undenatured whey protein (U-Lacp) exhibiting strong biological activity. Data on FIG. 3 (i.e. Table 3, below) indicate the relationship between the degree of denaturation of whey protein concentrate and the PFC immune response of the host.

powder) pH[37] or at pH 4.5[34,36,37], and decrease in light transmission of the solution[37]. In our studies we evaluated whey protein concentrate denaturation by the following methods:

Solubility measurements: After dispersion of a 3% protein solution in distilled water at room temperature and, in some cases, pH adjustment, the solution was stirred and then centrifuged for 20 minutes at 40,000×g. The protein content of the supernatant was determined by the Lowry method. Percent solubility was computed as the portion of total protein recovered in the supernatant fraction.

TABLE 3

INDIRECT INDICES OF DENATURATION OF WHEY PROTEIN CONCENTRATES

| | D-LACP. | SIGMA DENATURED | PROMOD | SAPRO | U-LACP | U-LAD |
|---|---|---|---|---|---|---|
| SOLUBILITY: (3%P) | 82.8% pH: 6.4 | 0% pH: 4.8 | 93.7% pH: 5.9 | 91.6% pH: 6.2 | 94.5% pH: 6.5 | — |
| LIGHT TRANSMITTANCE: (750 NM, 0.15%P) | 49.7% | 19.3% | 68.6% | 63.6% | 79.0% | — |
| SOLUBILITY INDEX: (pH 4.6, 3.0%P) | 72.8% | 0% | 84.7% | 83.8% | 92.0% | — |

The related Table 4, below, further indicates the lack of correlation between nutritional efficiency and denaturation of protein. In the natural state, the milk whey proteins have a definite conformation which, when exposed to heat above a certain critical level, is disrupted. In contrast to caseins, the whey proteins are Light transmittance: The initial 3% protein solution was diluted to 0.15% in distilled H$_2$O. The light transmittance of blank (distilled H$_2$O) and sample was measured at 750 nm with the spectrophotometer immediately after mixing.

TABLE 4

| | CASEIN | D-LACP | SIGMA DENATURED | PROMOD | SAPRO | U-LACP | U-LAD |
|---|---|---|---|---|---|---|---|
| Initial Weight (g): | 19.7 ± 0.2 | 19.4 ± 0.4 | 20.0 ± 0.5 | 23.6 ± 0.3 | 22.2 ± 0.2 | 18.8 ± 0.4 | 20.1 ± 0.3 |
| Final Weight (as % of initial wt.): | 124% ± 2 | 121.8 ± 0.8 | 122% ± 2 | 120% ± 2 | 121% ± 2 | 122% ± 1 | 121.6% ± 1.8 |
| Serum Protein (mg/dl): | 5.4 ± 0.1 | 5.7 ± 0.1 | 5.1 ± 0.1 | 5.3 ± 0.1 | 5.5 ± 0.1 | 5.8 ± 0.2 | 5.7 ± 0.9 |

Figure 3:
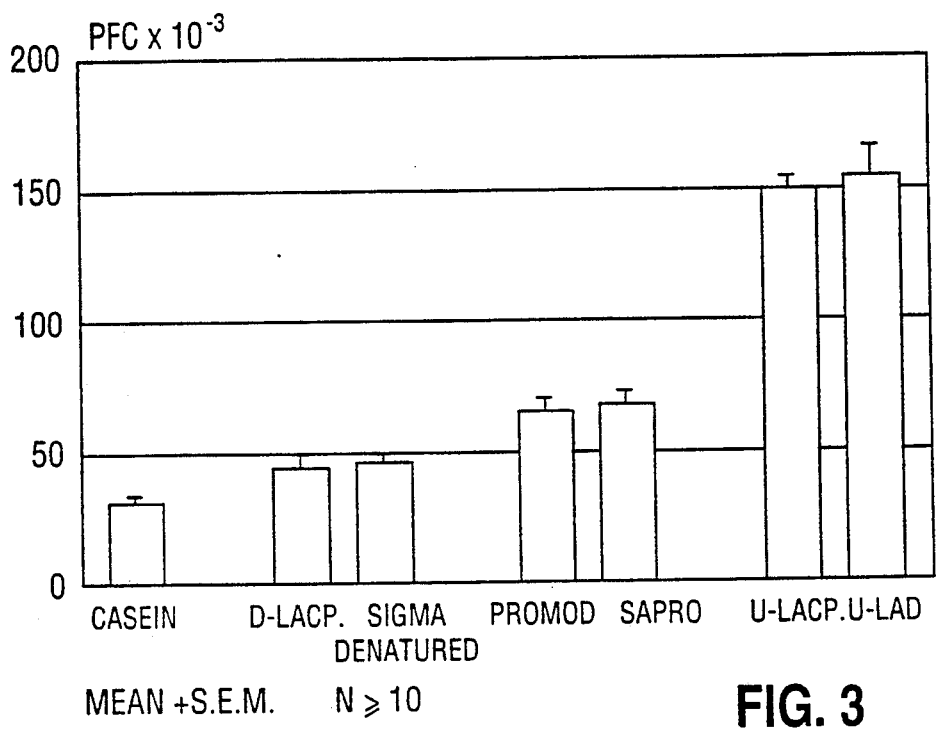
FIG. 3 and related Table 3 and 4 illustrate the effect of various sources of whey protein concentrate and casein (20 g/100 g diet) on spleen PFC response to $5 \times 10^6$ SRBC in mice.
Figure 4:
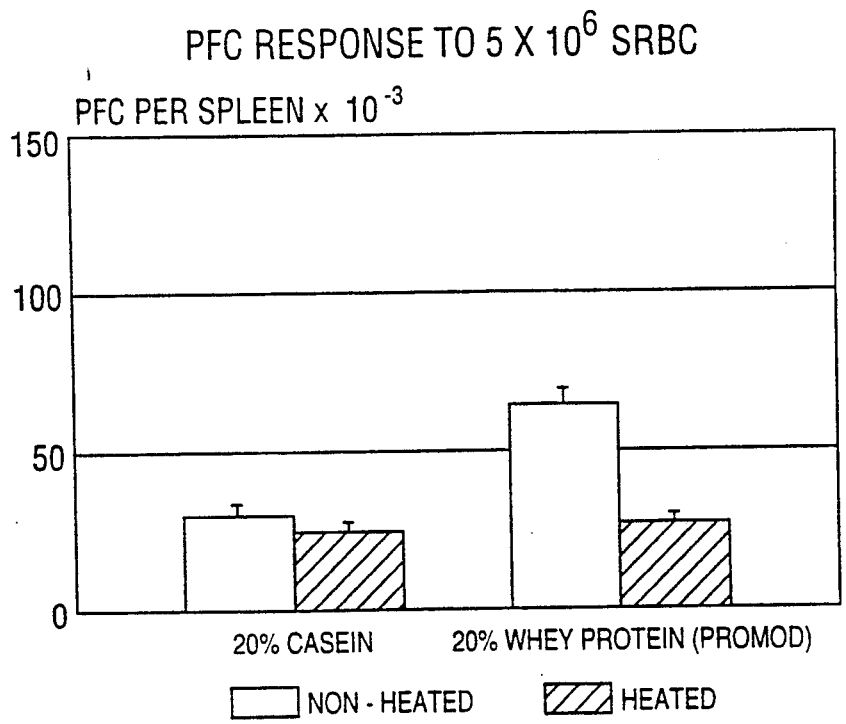
FIG. 4 and related Table 5 illustrates the effect of heat denaturation on the immunoenhancing property of whey protein concentrate.

D-Lacp = Denatured whey protein concentrate, Lacprodan-80 by "Danmark Protein", Denmark.
U-Lacp = Undenatured whey protein concentrate, Lacprodan-80 by "Danmark Protein", Denmark.
U-Lad = Pancreatic hydrolysate of undenatured whey protein concentrate by Nestle, Switzerland.
Promod = Whey protein concentrate by Ross Laboratories, Montreal.
Sapro = Whey protein concentrate by Saputo Ltd., Montreal.

rapidly denatured by heating. Denaturation of whey proteins causes unfolding of their globular structure to form a random coil conformation. In addition to heating, other processing treatment, e.g. pumping, mixing, aeration, vacuum evaporation and drying further promote protein denaturation[33]. The half cystine residues, frequent in some of the whey proteins[11], are connected by intramolecular disulfide bonds which contribute to the spatial configuration of the molecule and partly block unfolding of the molecule[34]. The free sulphydryl content of whey increases on heating due to an unfolding and subsequent exposure of buried sulphydryl groups, with rupture of the disulfide bonds in different whey proteins[35,36]. Heat denaturation unfolds and exposes the poorly soluble hydrophobic amino acid residues to water. The denaturation of whey protein is pH sensitive[36]. Hence, the extent of denaturation is normally assessed by loss of solubility at "natural" (intrinsic pH of an aqueous solution of the specific protein It is apparent from FIG. 3 that a positive relation exists between the undenatured state of whey protein concentrate in the diet and the intensity of the humoral immune response to SRBC. The level of immune response is not related to the nutritional efficiency of the whey protein concentrate but to its undenatured conformation (FIG. 3, and associated Table 3 and 4, above). Hence, the independence of the biological activity (immunoenhancement) from the nutritional aspect of the whey protein concentrate, shown in our previous short term experiments (FIGS. 1 and 2, Table 2, above) is confirmed. Further evidence of the inhibitory effect of heat denaturation on the immunoenhancing property of whey protein concentrate was obtained by heating a partially denatured whey protein concentrate (Promod). This procedure produced a significant drop in the immunoenhancing property of the diet without change in its nutritional efficiency (FIG. 4 and associated Table 5).

TABLE 5

| | Effect of three weeks of dietary treatment | | | |
|---|---|---|---|---|
| | CASEIN | | PROMOD | |
| C3H/HeN Mice | Non-heated | Heated | Non-heated | Heated |
| Initial weight (g): | 20.4 ± 0.2 | 23.8 ± 0.3 | 24.2 ± 0.3 | 21.8 ± 0.3 |
| Final weight (% of initial wt.): | 130% ± 2 | 120% ± 2 | 119% ± 2 | 127% ± 4 |
| Spleen weight (mg): | 92 ± 4 | 107 ± 5 | 104 ± 3 | 131 ± 7 |

TABLE 5-continued

| | Effect of three weeks of dietary treatment | | | |
|---|---|---|---|---|
| | CASEIN | | PROMOD | |
| C3H/HeN Mice | Non-heated | Heated | Non-heated | Heated |
| Protein (mg/dl): | 5.4 ± 0.1 | 5.5 ± 0.1 | 5.3 ± 0.1 | 5.6 ± 0.1 |

Promod non-heated vs. promod heated: p < .01
(90° C. for 10 minutes)
Promod non-heated vs. casein non-heated: p < .01
Mean ± S.E.M. (N = 10)

Preliminary heat treatment of the concentrated whey protein solution will not improve its overall digestibility; hence the whey protein concentrate used in the preparation of the pancreatic hydrolysate LAD was undenatured. The absence of cysteine in the free amino acid fraction of LAD is consistent with the knowledge that pancreatic trypsin does not hydrolyse the disulfide cross-linkage[38] characteristic of the native whey protein which is instead split in the process of denaturation[34-36,39-41].

LAD is composed of small peptides (approx 80%) and of free acid amines (approx. 20%). The molecular weights of peptides varies between 450 and 1000. A large percentage of essential or nutritionally important acid amines are present in free form: Lys (63%), Arg (39%), His (18%), Met (59%), Ile (22%), Leu (32%), Tyr (80%), Phe (56%) and Trp (99%). LAD is an experimental product which should not be used for clinical treatment of humans.

DIETARY WHEY PROTEIN AND PNEUMOCOCCAL INFECTION

Because our studies had shown that dietary protein type influences the humoral immune response, we then proceeded to investigate the effect of U-Lacp in diet on the resistance of mice to pneumococcal infection. Pneumococci represent the group of encapsulated high virulence organisms against which the body employs a humoral immune response. C3H/HeJ mice fed a diet containing 20 g U-Lacp/100 g diet showed improved survival after i.v. infection with *Streptococcus pneumoniae* type 3 as compared to similarly infected mice fed a 20 g C/100 g diet of similar nutritional efficiency[10] (Table 6 below).

On the basis of our various studies, it was shown that the enhanced resistance of mice fed the whey protein diet to infection with *Streptococcus pneumoniae* type 3 was independent of the weight of the animal at the time of infection and the weight gained before infection (animals were fed the diets for 2 weeks prior to infection).

TABLE 6

SUSCEPTIBILITY TO TYPE 3 *S. PNEUMONIAE*
OF THREE SERIES OF MICE FED
DIETS OF VARIOUS PROTEIN TYPES[1]

| | Ratio of alive:dead mice | | | | | |
|---|---|---|---|---|---|---|
| Days | Experiment 1 | | Experiment 2 | | Experiment 3 | |
| Post-Infection[2] | C | L | C | L | C | L |
| 0 (10²) | 8:0 | 8:0 | 10:0 | 10:0 | 10:0 | 10:0 |
| 2 | 8:0 | 8:0 | 10:0 | 10:0 | 10:0 | 10:0 |
| 3 | 7:1 | 8:0 | 10:0 | 10:0 | 10:0 | 10:0 |
| 4 | 7:1 | 8:0 | 9:1 | 10:0 | 9:1 | 10:0 |
| 9 (10³) | 7:1 | 8:0 | 9:1 | 10:0 | 9:1 | 10:0 |
| 11 | 7:1 | 8:0 | 9:1 | 10:0 | 9:1 | 10:0 |
| 12 | 7:1 | 8:0 | 5:5 | 9:1 | 8.2 | 10:0 |
| 13 | 6:2 | 8:0 | 4:6 | 9:1 | 8:2 | 10:0 |
| 14 | 5:3 | 8:0 | 4:6 | 9:1 | 7:3 | 9:1 |
| 40 | 5:3 | 8:0 | 4:6 | 9:1 | 7:3 | 9:1 |

[1]Mice were infected after 2 wk treatment with casein diet (C) (20 g casein/100 g diet), or lactalbumin diet (L) (20 g/100 g).
[2]Injected i. v. in 1% FCS-Ringer; 9 days after infection with 10² pneumococci the surviving mice were infected with a dose of 10³ pneumococci.
C = Casein
L = Lactalbumin = Whey Protein Concentrate.
Overall mortality is 36% in the C fed groups and this is significantly higher (P = 0.002) than that of the L fed mice which is 7.1%.

MECHANISM RESPONSIBLE FOR THE IMMUNOENHANCING EFFECT OF WHEY PROTEIN CONCENTRATE IN DIET

Over the past few years we have attempted to identify the changes induced by dietary protein type which might directly or indirectly affect the humoral immune responsiveness. In mice not challenged with an immunogenic stimulus, the type of protein in the diet was found to have little or no effect on a variety of parameters examined. Thus, body growth, food consumption, serum protein, minerals and trace metals, circulating leukocytes and more specifically, the genesis of bone marrow B lymphocytes were all within normal limits[5-10,31]. These findings confirm that at 20 g/100 g diet concentration, the proteins provide an adequate daily supply of essential amino acids for the growing mice. The only significant effect of protein type was found to be a change in plasma amino acid profile, which essentially conformed to the amino acid composition of the ingested protein, with the notable exception of cysteine (Tables 7 and 8, below).

We were particularly intrigued by the finding that, in spite of an 8- fold higher cysteine content in WPC, the plasma level of cysteine in WPC diet-fed mice was not different from that in their C diet-fed counterparts. The fate of the excess cysteine was a matter of interest. Dietary cysteine is a rate limiting substrate for the synthesis of glutathione (GSH) which is necessary for lymphocyte proliferation. GSH is dependent upon the supply of cysteine which is derived from dietary protein. The redox state of the lymphocyte can modulate the intracellular concentration of cyclic GMP, which is known to be intimately involved in lymphocyte proliferation.

Our studies have shown that the observed enhancement of the immune response is associated with greater production of splenic glutathione in immunized mice fed whey protein in comparison to mice fed a casein or cysteine enriched casein diet. The efficiency of dietary cysteine in inducing supernormal glutathione levels is greater when it is delivered in the whey protein than as free cysteine.

TABLE 7

AMINO ACID COMPOSITION OF TEST PROTEIN[a]
(g/100 g protein)

| AMINO ACID | CASEIN | WHEY PROTEIN CONCENTRATE |
|---|---|---|
| Phenylalanine | 5.3 ± 0.2 | 3.4 ± 0.3 |
| Tryptophan | 1.4 ± 0.2 | 2.1 ± 0.0 |
| Glycine | 2.0 ± 0.1 | 2.0 ± 0.2 |
| Serine | 6.2 ± 0.5 | 5.2 ± 0.4 |
| Leucine | 10.0 ± 0.4 | 10.4 ± 0.7 |
| Isoleucine | 6.0 ± 0.6 | 6.1 ± 0.8 |
| Valine | 7.1 ± 0.3 | 5.8 ± 0.8 |
| Methionine | 2.9 ± 0.2 | 2.1 ± 0.3 |
| Cysteine | 0.3 ± 0.1 | 2.3 ± 0.3 |
| Aspartic acid | 7.3 ± 0.1 | 10.7 ± 0.7 |
| Glutamic acid | 22.9 ± 0.2 | 18.8 ± 0.7 |
| Histidine | 3.0 ± 0.1 | 2.0 ± 0.2 |
| Tyrosine | 6.0 ± 0.1 | 3.0 ± 0.4 |
| Proline | 11.6 ± 0.4 | 6.1 ± 0.7 |
| Arginine | 4.0 ± 0.1 | 2.8 ± 0.3 |
| Alanine | 3.1 ± 0.3 | 4.9 ± 0.4 |
| Lysine | 8.2 ± 0.1 | 9.2 ± 0.5 |
| Threonine | 4.6 ± 0.3 | 6.8 ± 1.3 |

[a]Value expressed as Mean ± S.D. of data from reliable sources.

TABLE 8

EFFECT OF DIETARY PROTEIN TYPE ON PLASMA AMINO ACID PATTERNS

| Amino Acid | Lactalbumin 20 g % (whey protein concentrate) nmol/ml | Casein 20 g % | P-value |
|---|---|---|---|
| Isoleucine | 90 ± 5 | 95 ± 8 | — |
| Leucine | 125 ± 5 | 113 ± 4 | — |
| Valine | 232 ± 10 | 278 ± 13 | 0.025 |
| Methionine | 72 ± 3 | 92 ± 6 | 0.025 |
| Cystine | 37 ± 3 | 37 ± 3 | — |
| Phenylalanine | 51 ± 1 | 75 ± 4 | 0.0005 |
| Tyrosine | 55 ± 2 | 83 ± 5 | 0.005 |
| Threonine | 310 ± 7 | 223 ± 2 | 0.0005 |
| Tryptophan | — | — | — |
| Lysine | 301 ± 6 | 323 ± 7 | — |
| Histidine | 50 ± 1 | 64 ± 4 | 0.005 |
| Arginine | 61 ± 4 | 92 ± 6 | 0.005 |
| Glycine | 142 ± 7 | 144 ± 7 | — |
| Serine | 120 ± 8 | 132 ± 4 | — |
| Alanine | 437 ±1 18 | 382 ± 19 | 0.05 |
| Proline | 52 ± 5 | 117 ± 10 | 0.0005 |
| Aspartic Acid | 24 ± 2 | 16 ± 1 | 0.005 |
| Glutamic Acid | 65 ± 2 | 44 ± 4 | 0.005 |

Mean ± SD.

METHOD TO INCREASE TISSUE GLUTATHIONE

Figure 5:
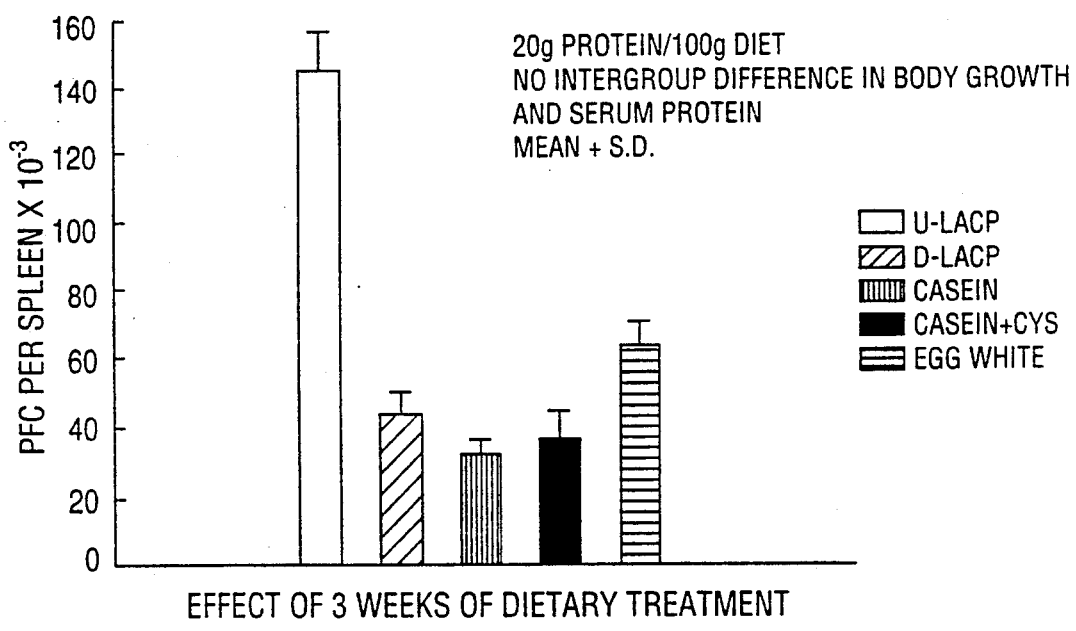
FIG. 5 illustrates plaque forming cells/spleen (PFC) on the day (day 5) showing peak production of PFC following immunization of C3H/HeN mice with $5 \times 10^6$ SRBC.
Figure 6:
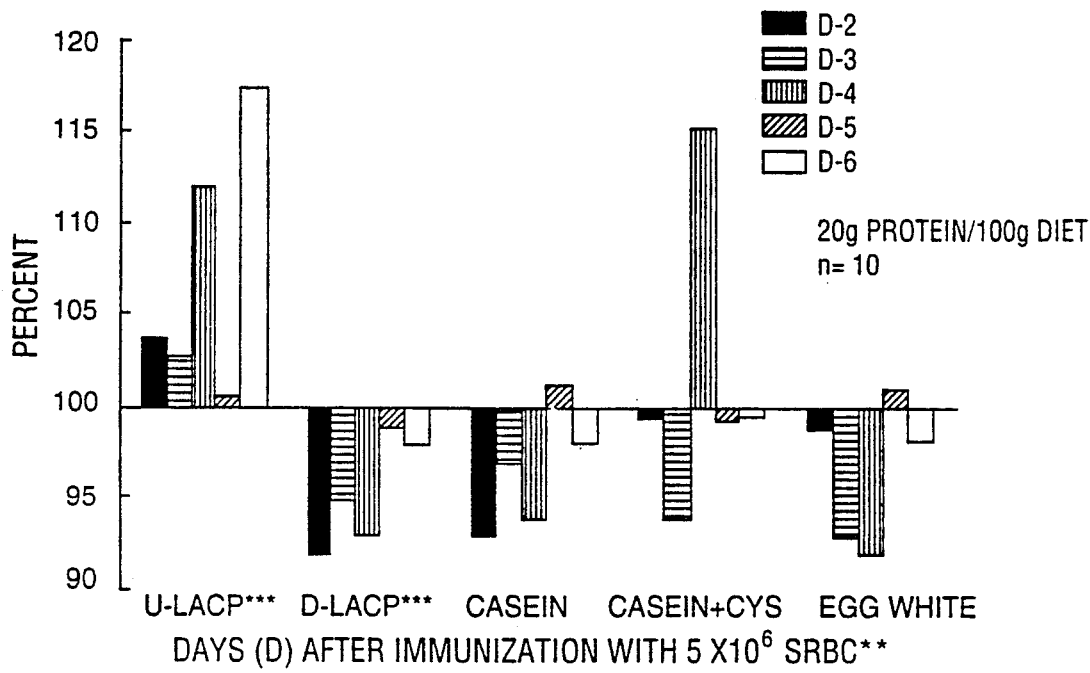
FIG. 6 illustrates spleen glutathione as percent of values of unimmunized C3H/HeN male mice fed with the corresponding diet for three weeks.

We further explored the interaction of dietary protein, GSH and the host immune response We investigated whether a different protein source such as egg white, with the same high level of cysteine as whey protein concentrate (Table 9, below), had a similar effect in promoting higher GSH tissue content We already knew that an egg white protein diet does not enhance the host immune response above average. Whereas the static GSH level in spleen was found unaltered by U-Lacp feeding for three weeks, our studies in young adult C3H mice showed that enhancement of spleen cell immune response to SRBC (FIG. 5) is associated with sustained elevation of splenic GSH during the antigen-driven clonal expansion of the lymphocytes in U-Lacp (undenatured whey protein)-fed mice in comparison to a pattern of decline observed in spleen GSH levels in mice fed either of the nutritionally equivalent D-Lacp (denatured whey protein), casein, cysteine enriched casein, or egg white protein diets (FIG. 6). The latter four groups also exhibited a lower immune response (FIG. 5). Administration of S-(n-butyl) homocysteine sulfoximine, which reduces the splenic glutathione level by half, produces a marked drop in the humoral immune response of whey protein (U-Lacp) diet-fed mice. This is further evidence of the important role of glutathione in the immunoenhancing effect of dietary whey protein (FIG. 7).

TABLE 9

AMINO ACID COMPOSITION
(g/100 g protein)

| Amino Acid | Whey Protein Concentrate* | Egg White Protein** |
|---|---|---|
| Aspartic acid | 11.3 | 7.9 |
| Threonine | 7.2 | 4.4 |
| Serine | 6.1 | 7.9 |
| Glutamic acid | 20.1 | 14.1 |
| Proline | 6.6 | 3.8 |
| Glycine | 2.0 | 3.7 |
| Alanine | 5.4 | 7.6 |
| Valine | 6.5 | 7.8 |
| Isoleucine | 6.7 | 6.5 |
| Leucine | 11.2 | 8.8 |
| Tyrosine | 2.9 | 4.2 |
| Phenylalanine | 3.1 | 6.4 |
| Lysine | 9.5 | 6.0 |
| Histidine | 1.9 | 2.2 |
| Arginine | 2.7 | 5.9 |
| Methionine | 2.2 | 3.9 |
| Cysteine | 2.4 | 2.4 |
| Tryptophan | 1.7 | 1.5 |

*Lacprodan-80 from Danmark Protein A/S, Copenhagen, Denmark, 1986; used in our experiments.
**Values calculated from "Amino Acid Content of Foods", U.S.D.A., 1957. Values from cysteine analyzed by Sigma on samples used = 2.38 g/100 g protein and in our laboratory = 2.4 g/100 g protein.

Tissue Glutathione Assay

Ninety milligrams of mouse heart or layer were homogenized in 5-sulfosalicylic acid (5% w/v). Homogenates are centrifuged for 5 minutes in a microfuge at 10,000×g. The assay is carried out using the supernatants on the same day according to the method of Anderson[72]. Values are expressed as μmol/g wet tissue (FIGS. 8 and 9).

After three months on either diet initiated at age 17 months, GSH content was found to be higher in the liver and heart of U-Lacp (undenatured whey protein) fed mice compared to the D-Lacp (denatured whey protein), casein, egg white protein or Purina diet-fed counterparts (FIGS. 8 and 9). The GSH values in heart and liver of mice fed Purina laboratory chow was similar at age 10 weeks, 17, 20, 21 months The U-Lacp diet appears to enhance the GSH content of heart and liver above "normal" values after 3 and 4 months of continuous feeding (FIGS. 8 and 9).

In conclusion, after three weeks on the U-Lacp diet, spleen GSH content is increased during the antigen driven clonal expansion of the lymphocytes in young adult C3H/HeN mice as compared to a decline in controls fed D-Lacp, casein or egg white protein diets (FIG. 6). In old C57BL/6N1A mice, long term feeding of U-Lacp diet results in a moderate but sustained increase in liver and heart GSH levels (FIGS. 8 and 9). The GSH enhancing activity of WPC is restricted to its undenatured form (U-Lacp). This property is not solely due to the high cysteine content of WPC because another protein source with similar cysteine content (egg white) (see Table 9) does not exhibit this biological activity. This property of U-Lacp does not depend specifically on its nutritional efficiency as evaluated by body weight, serum proteins, and food consumption, but appears to depend on the primary, secondary and tertiary structure of the protein in its native form.

Some of the previously discussed methods of increasing intracellular levels of glutathione concentration are either toxic[64] or dangerous owing to the risks related to the initial phase of glutathione depletion[70,71]. The methods involving the use of gamma-glutamyloyst-(e)ine[67], athiazolidine[69] or glutathione esters[68] (U.S. Pat. No. 4,784,685) offer an interesting possibility for short term intervention. However, their long term effectiveness in producing sustained elevation of cellular glutathione has not been shown, nor has the possible toxicity of their long term use been disproved. Indeed, glutathione and glutathione disulfide were found to be positive in the most commonly used short term tests for carcinogenicity and mutagenicity[64]. Relevant to our invention are recent data indicating specifically that a lack of the GSH precursor, cysteine, rather than a decrease in biosynthetic enzyme activities is responsible for the deficiency of GSH noted in aging animals[73]. Similarly, the fall in cytosolic GSH in the liver of chronic ethanol fed rats does not appear to be caused by a limitation in the capacity of gamma-glutamyloysteine synthetase activity[74].

Data in FIGS. 8 and 9 show that the concentration of liver and heart glutathione in control Purina fed mice remains very constant over time. On the other hand a moderate but sustained elevation of tissue GSH was noted in mice fed the nutritionally equivalent whey protein (U-Lacp) diet. Only minuscule quantities of glutathione and no breakdown products that can be readily attributed to glutathione are excreted in urine[75]. The magnitude of change in cellular glutathione concentration that can be achieved may be quite limited, perhaps reflecting the critical importance of this molecule and the attendant tight regulatory control. Glutathione itself serves as a negative feedback on the GSH synthetic enzymes, which obviously limits cellular capacity to increase GSH concentration[42]. Glutathione reductase maintains GSH in its predominant reduced form ($\geq 90\%$). This serves both to maintain this functional state and also to control cellular concentration since reduced glutathione (GSH) cannot cross the membrane, whereas the oxidized form (GSSG) can and does afflux, resulting in decreased total glutathione. Besides these enzymes, gamma glutamyltranspeptidase (GGT) is important in GSH metabolism. GGT serves as a salvage pathway for glutamyl moieties at the cell membrane level, passing them back into the cytosol to be used in GSH synthesis. Increased activity of this enzyme has been associated with elevated GSH concentration in a number of cell lines and malignant tissues[76,77].

The effects of a small increment in cellular GSH may be greater than expected. For example, there are many reports of human and murine tumor cell lines selected in vitro for resistance to a variety of chemotherapeutic agents. In a number of these cell lines cellular GSH is increased consistently by 2-fold compared to the drug sensitive parental cell line, despite the fact that the level of drug resistance is often much greater, e.g. as much as 30-fold[77-79]. In these cell lines, depletion of cellular GSH by selective inhibition of synthesis restores drug sensitivity to the resistant cells. This is effective only if the GSH depletion is maintained throughout the drug-treatment period.

Given the fact that cellular GSH is very tightly regulated, that a 2- fold increase may be maximal, and that the effect of small increments in GSH may be amplified by a variety Of GSH-utilizing enzymes (e.g. glutathione peroxidase, glutathione-S-transferase), the reproducible change in GSH concentration observed in animals fed the whey-rich diet is likely to have biological importance. The chronic nature of this augmentation may contribute significantly to this effect.

A METHOD TO INHIBIT THE GROWTH OF CHEMICALLY INDUCED COLON CANCER

Our findings show that in mice fed a casein diet the number and size of DMH induced colon carcinoma were reduced by a factor of 0.3 and 0.4 respectively in comparison to Purina fed controls (Table 10, below). However, in mice fed the whey protein diet with similar nutritional efficiency the number and size of DMH-induced colon carcinoma were reduced four fold in comparison to the Purina fed controls (Table 10, below). DMH- induced colon tumors appear to be similar to those found in humans as far as type of lesions and chemotherapeutic response characteristics are concerned[93,94]. The superiority of the anti-cancer effect of whey protein in comparison to casein has been reported in our previous study. About 80% of the proteins in bovine milk are caseins and the remaining 20% are whey proteins[95,96]. In addition, using the traditional process of preparing casein, the amount of whey protein co-precipitated along with the casein varies from about 40 to 60% of the total amount of whey protein present in the milk[97]. Therefore it is conceivable that the minor anti-cancer effect seen with casein could be due to the relatively (to caseins) small amount of whey protein co-precipitated with it. It is apparent from the above described studies that the antitumor activity of the dairy products is in the protein fraction and more specifically, as our invention demonstrates, in the whey protein component of milk.

TABLE 10

Effect of dietary milk protein on animal growth and tumour development in A/J mice treated with the carcinogen 1,2-Dimethylhydrazine.

|  | Whey Protein 28 Weeks[a] | Casein 28 Weeks[a] | Purina 28 Weeks[a] | Pur/Whey 20/8 Weeks[b] | Pur/Cas 20/8 Weeks[b] |
|---|---|---|---|---|---|
| Initial Weight[c] (g) | 21.7 ± 0.5 | 21.5 ± 0.7 | 21.9 ± 0.8 | 21.9 ± 0.4 | 22.0 ± 0.7 |
| Final Weight[c] (g) | 21.5 ± 0.3 | 21.8 ± 0.4 | 19.7 ± 0.7 | 21.3 ± 1.0 | 21.0 ± 0.6 |
| Number of Tumours[c] | 8.4 ± 1.5 | 24.7 ± 3.0 | 35.9 ± 2.6 | 15.1 ± 3.2 | 21.7 ± 4.3 |
| Tumour Area[c] | 38.8 ± 6.4 | 90.9 ± 10.6 | 160.0 ± 11.4 | 47.9 ± 10.4 | 77.7 ± 10.9 |

ANOVA: solid line(s) connect those means not significantly different ($p < 0.05$).
Group    Whey    Pur/Whey    Pur/Casein    Casein    Purina

TABLE 10-continued

Effect of dietary milk protein on animal growth and tumour development in A/J mice treated with the carcinogen 1,2-Dimethylhydrazine.

| | Whey Protein 28 Weeks[a] | Casein 28 Weeks[a] | Purina 28 Weeks[a] | Pur/Whey 20/8 Weeks[b] | Pur/Cas 20/8 Weeks[b] |
|---|---|---|---|---|---|
| Number of Tumours | | | | | |
| Tumour Area | | | | | |

[a]Mice treated with DMH for 24 weeks, and then sacrificed 4 weeks later.
[b]Mice treated with DMH for 24 weeks, and then sacrificed 4 weeks later. They were maintained on Purina Mouse Chow for 20 weeks and then switched to either Whey Protein or Casein diet for the remaining 8 weeks.
[c]Mean ± SEM.

SURVIVAL STUDIES: THE BIOLOGICAL ACTIVITY IS DEPENDENT ON THE UNDENATURED CONFORMATION OF WPC

(a) Survival of Old Mice During a Limited Time Period

Figure 10:
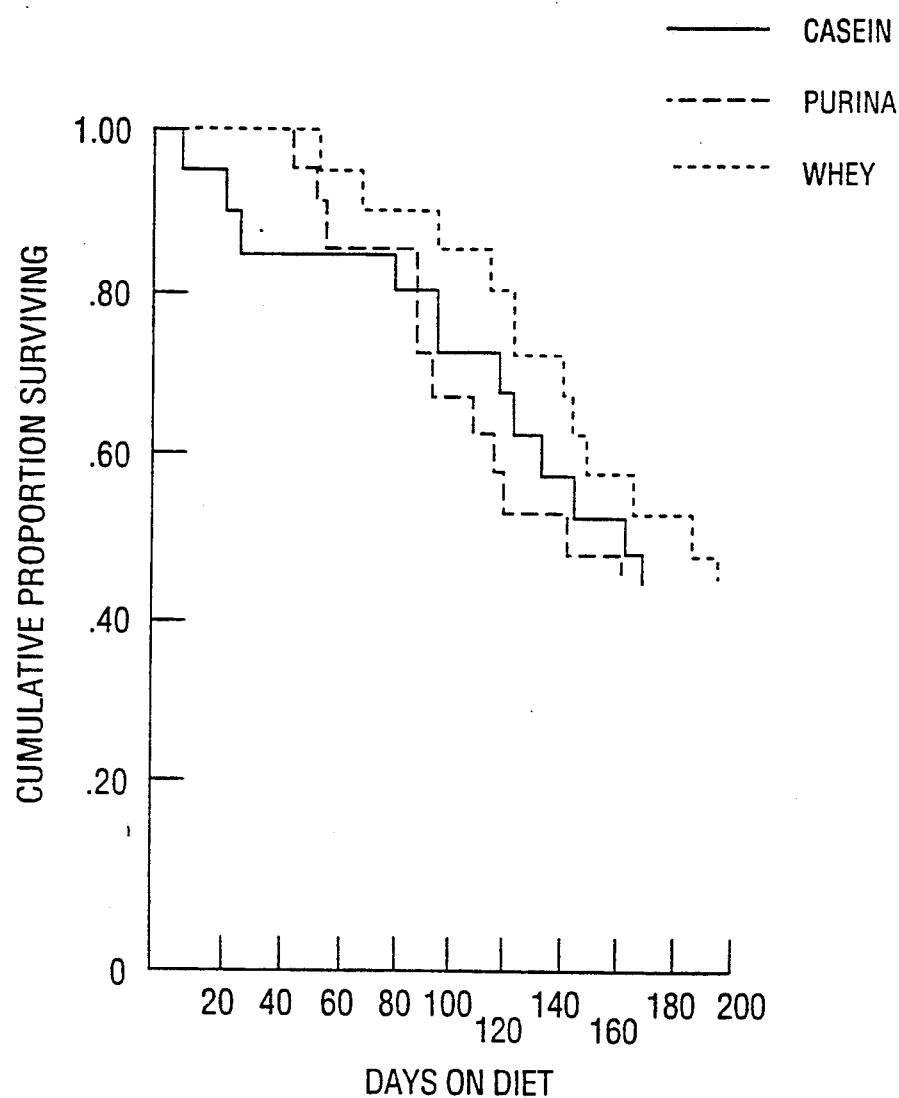
FIG. 10 illustrates the survival curves of 2 month old male C57/BL/6NIA mice fed casein, Purina Mouse Chow and whey protein.

Our study shows that the mean survival time, over a limited observation period of 6–7 months ending when 55% of male C57BL/6N1A mice were dead, is increased by about 30% in mice commenced on the undenatured whey protein (U-Lacp) diet at the onset of senescence (age 21 months) in comparison with "controls" fed the nutritionally equivalent Purina mouse chow. The survival curve of Purina fed mice was very similar to that of casein diet-fed mice (FIG 10). However, in the subsequent four months, mice on undenatured whey protein diet were switched to a denatured whey protein concentrate (D-Lacp) diet. During this period, the time of death of the remaining whey protein diet-fed mice became similar to that of their casein diet or Purina-fed counterparts. Throughout the study repeat bioassays of PFC formation confirmed the correlation between host immunoenhancement and undenatured state of WPC in diet as indicated in FIG. 3. In the second part of the study, when the difference between survival curves began to narrow, the immunoenhancing property of WPC was absent although its nutritional quality was preserved (D-Lacp). Throughout the entire study no significant intergroup difference was seen in calorie intake, and body weight. Since longevity is dependent primarily upon the genome of the individual it is unlikely that delayed mortality over a limited period of time would have influenced overall longevity. However, at least in terms of the immunoenhancing effect of the diet, this study could be regarded as a single direction cross-over from test (U-Lacp) to control (D-Lacp) diets, showing that the biological activity of WPC on survival of old mice is dependent upon its undenatured state and correlating directly with the PFC assay used in our study (as illustrated in FIG. 3).

(b) Short and Long Term Survival of Mice with DMH-Induced Colon Cancer

In DMH treated mice we noticed a difference between mortality by the 28 weeks end point and the survival time to the end of the experiment in relation to dietary protein type. During the first seven months of study, the mice fed undenatured whey protein (U-Lacp) had no death as compared to a 33% mortality observed towards the end of this period in the casein and Purina groups. In the subsequent four months mice on whey protein were fed denatured whey protein (D-Lacp). During this latter period the D-Lacp diet appeared to have no favourable effect on survival in comparison to the casein diet (Table 11, below). Throughout the study repeat bioassays of spleen PFC were done to document the physiologic effects of the diets on immune function as reported previously and the stability of these effects. The immunoenhancing effect of the U-Lacp diet was consistently confirmed for the first 7 months of the study; however, in the following four months (D-Lacp), the immunoenhancing effect previously observed in mice fed the U-Lacp diet was absent. The values of PFC response in relation to either the U-Lacp diet or the D-Lacp diet were consistent with those presented in FIG. 3. This study therefore confirms the hypothesis that the biological activity of WPC on survival of tumor bearing mice is dependent upon its undenatured state correlating directly with the PFC assay used in our study.

TABLE 11

Effect of dietary milk protein on short and long term survival in A/J mice treated with the carcinogen 1,2-Dimethylhydrazine for 24 weeks.

| | DIETARY GROUP[b] | | |
|---|---|---|---|
| | Whey Protein[d] | Casein | Purina |
| Mortality[a] at 28 weeks | 0% | 33% | 33% |
| Survival time[c] in weeks. | 40 | 41 | 30 |

[a]Significance by Chi Square analysis: Whey Protein vs. Purina vs. Casein $p < 0.05$.
[b]Originally 12 mice per group.
[c]Survival time in weeks from the first dose of carcinogen. Whey protein and Casein differ significantly from Purina, Mantel-Cox test $p < 0.01$.
[d]Undenatured Whey Protein used from weeks 3 to 28. Denatured Whey Protein used from week 28 until end.

Synergistic Role of Vit. $B_2$, $B_1$ in the Immunoenhancing Effect of Dietary Whey Protein Concentrate While whey protein represent an optimal source of cysteine, the rate limiting substrate for the biosyntheses of GSH, Vit. $B_2$ and $B_1$ are important elements in the function of the GSH redox cycle.

Glutathione (GSH) status in tissues is maintained mainly in the reduced state (GSH:GSSG, 250), which is achieved by the efficient GSH peroxidase and reductase system coupled to the NADP+/NADPH redox pair. Endogenous toxic $H_2O_2$ is reduced to $H_2O$ through the oxidation of GSH to GSSG catalyzed by GSH peroxidase At the expense of cellular NADPH, GSSG is effectively reduced back to GSH by NADPH:GSSG reductase, thus maintaining thiol balance. As a result, GSSG reductase has a great capacity to protect cells against oxygen toxicity from endogenous active oxygen species.

Vit. $B_1$ (thiamin) is involved in the transketolase reaction of the pentose phosphate shunt yielding NADPH and pentose.

Vit. $B_2$ (riboflavin): The coenzyme derivatives of riboflavin, flavin mononucleotide (FMN) sequentially from riboflavin. Vit $B_2$ deficient animals exhibit marked decreases in activities of FMN and FAD-requiring enzymes such as GSH reductase.

In this sense, it is conceivable that all these water soluble vitamins naturally present in whey, play an essential role for optimal function of the GSH redox cycle particularly when whey protein intake, as shown in our experiments, has produced higher level of GSH synthesis and storage in the tissues.

Figure 11:
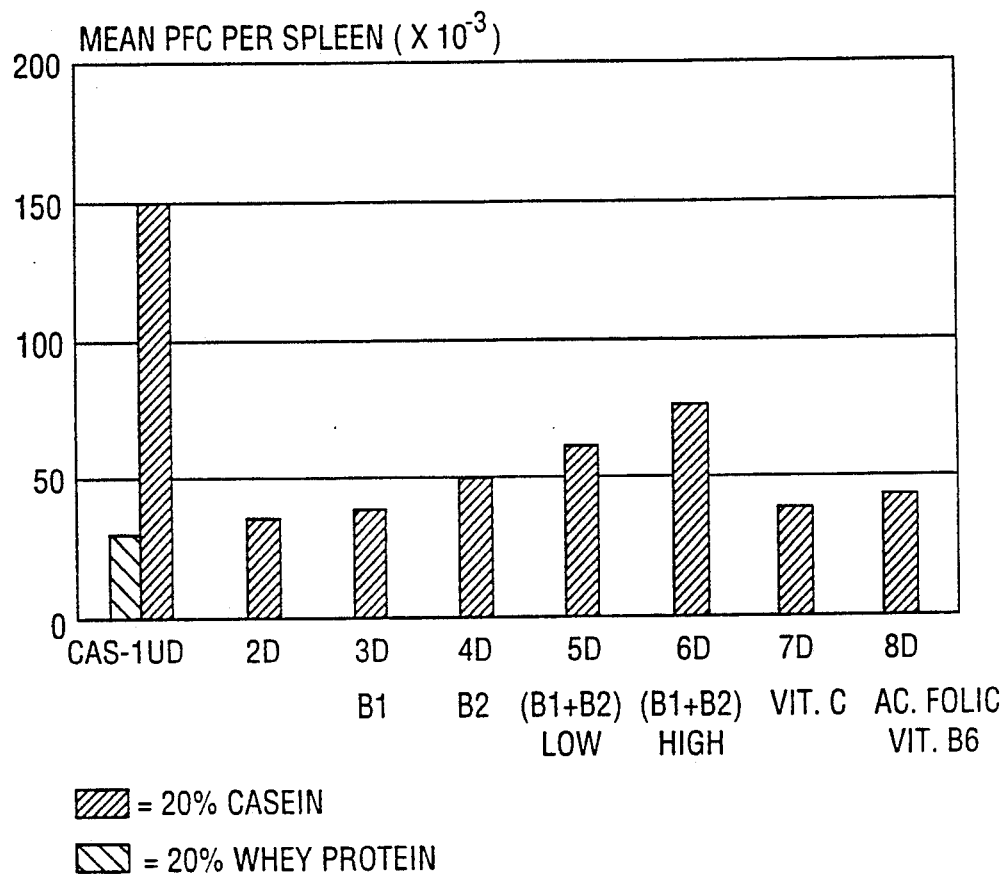
FIG. 11 illustrates the effect of 26 days dietary treatment on PFC response to SRBC.

The present studies (FIG. 11) show that dietary levels of Vit. $B_1$, $B_2$ slightly above recommended allowance (Table 12, diets 5, 6; below) contribute to the immunoenhancing effect of dietary whey protein concentrate. Whey protein, by providing optimal bioavailability of the limiting substrate (cysteine) enhances the synthesis and storage of GSH. On the other hand, higher than normal intakes of Vit. $B_1$ and $B_2$ appears to be necessary to maintain the GSH redox cycle at a level higher than normal, thus allowing the development of a better than normal, immune response to SRBC. Individually the effect of each of the vitamins in whey protein fed mice is limited; however, their synergistic effect on the immune response of whey protein fed mice is apparent (FIG. 11, diets 5, 6 and diet 1). The same vitamins are ineffective on the immune response of casein diet-fed mice. Although all these water-soluble vitamins are present in whey, it is interesting to note that the main natural source of the single most effective vitamin, riboflavin, is whey to which Vit. $B_2$ gives its characteristic color.

reported in The Commonwealth Bureau of Animal Nutrition's NUTRITION ABSTRACTS AND REVIEWS, Volume 28, No. 2 (1958), the RDA for riboflavin is about 0.6 mg per 1000 Cal for women and about 0.5 mg per 1000 Cal for men.

In the stomach, whey is separated from milk by the action of gastric juice. It is conceivable that the transit and absorption of the water-soluble vitamins and proteins of whey occur faster than those of the protein (casein) and vitamin constituents of the milk coagulum (curd). Hence the whey protein and vitamins including the vitamins $B_1$ and $B_2$ could enter the systemic circulation at a different rate than that of other milk constituents and express their synergistic effect on the immune system and the GSH redox cycle.

The immunoenhancing and the other specific biological properties of dietary whey protein described in this application, are heat labile and dependant upon the undenatured (native) state of the protein (which can also be affected by vigorous shaking, solvents, extreme ph changes, etc.) and are independent of its nutritional quality which is unaltered by the process of denaturation.

Unlike most other commercially available when protein which are denatured, the whey protein used in Our experiments, produced in Denmark (Lacprodan - 80) is 90% undenatured (U.D. in FIG. 11). This protein displays the greatest tendency to denature under heat thus exposing its free sulfhydryl group. When experiments

TABLE 12

| VITAMINS (mg/100 g Diet) | VITAMIN CONTENT OF TEST DIETS | | | | | | |
|---|---|---|---|---|---|---|---|
| | (Diet 1) | Diet 3 | Diet 4 | Diet 5 | Diet 6 | Diet 7 | Diet 8 |
| VIT. B1 | 0.34 | 1.42 | | 0.9 | 2.7 | | 1.0 |
| VIT. B2 | 0.38 | | 1.47 | 0.9 | 2.7 | | 0.6 |
| VIT. B6 | 0.26 | | | | | | 0.7 |
| AC. FOLIC | 0.063 | | | | | | 0.1 |
| VIT. C | 53.3 | | | | | 118.3 | |

In conclusion, dietary intake of Vit $B_1$ and particularly $B_2$ above recommended daily allowance contribute to the development of enhanced immune response in whey protein fed animals: Vitamin $B_2 + B_1$ appears to produce the strongest effect. When intake of these vitamins is at or slightly below these levels, growth and animal appearance are normal, but the response to immune challenge is below the maximum potential of whey protein fed mice. The whey protein composition according to the invention comprises in combination said WPC together with vitamins $B_1$ and $B_2$ in amount of 1.5 to 2.0 mg $B_1$ and 1.5 mg to 2.0 mg $B_2$ per 100 g diet.

As reported in Nutrition Reviews' PRESENT KNOWLEDGE IN NUTRITION, The Nutrition Foundation, Inc. (1984), the current U.S. recommended dietary allowance (RDA) for Vitamin $B_1$ (thiamin) is 0.5 mg per 1000 kcal. This amount is based on assessments of varying levels of dietary thiamin on clinical signs of deficiency, on excretion of thiamin and its metabolites, and on ETKA and TPP effects. The present RDA for thiamin is 0.5 mg per 1000 kcal.

The allowance for Vitamin $B_2$ (riboflavin) in males 11 to 51 plus years in age ranges from 1.2 to 1.5 mg per day and for women from 1.2 to 1.3 mg, according to estimates of the Food and Nutrition Board of the National Academy of Sciences. Levels are to be increased by 0.3 mg during pregnancy, by 0.5 mg during lactation and possibly should be related to energy expenditure. As were done using a batch of w.p.c. received after a long surface transport from Denmark through the U.S. in exceptionally hot and humid weather (summer 1988), the immunoenhancing property of w.p.c was lost (FIG. 11, 2d-8d). These experiments, while indicating the synergistic role of vit. $B_1$ and $B_2$, in the immunoenhancing effect of the diet, also show the negative effect of a presumably partially denatured whey protein. Previous studies have shown that the immunoenhancing property of dietary whey protein is probably related to an optimal intracellular transport and availability of the cysteine which is a limiting precursor for glutathione synthesis. It is conceivable that partial denaturation of this protein had brought about the loss of its specific biological property by altering GSH synthesis, without an effect on its nutritional quality.

Although specific preferred embodiments of the invention have been described above with reference to the accompanying drawings, it will be apparent that the invention is not limited to those precise embodiments, and that many modifications and variations could be effected therein by one statement in the art without departing from the spirit or scope of the invention as defined in the appended claims.

REFERENCES

1. BARICELLI, G.C. De seri facultatibus, et usu, opusculum secundum. Scorriggium, Publ. Naples, Italy, p. 105-147, 1603.
2. HOFFMAN, K.F. Zur geschichte der molkenkuren, insbesondere im 17, 18 und 19 Jahrhundert, Med. Monatschr. 15: 411-416, 1961.
3. BIRT, D.F., BAKER, P.Y., HRUZA, D.S. Nutritional evaluation of three dietary levels of lactalbumin throughout the lifespan of two generations of syrian hamsters. J. Nutrit. 112: 2151-2160, 1982.
4. BIRT, D.F., SCHULDT, G.H., SALMASI, S. Survival of hamsters fed graded levels of two protein sources. Lab. Animal Sci. 32: 363-366, 1982.
5. BOUNOUS, G., STEVENSON, M.M., KONGSHAVN, P.A.L. Influence of dietary lactalbumin hydrolysate on the immune system of mice and resistance to Salmonellosis. J. Infect. Dis. 144: 281, 1981.
6. BOUNOUS, G., KONGSHAVN, P.A L. Influence of dietary proteins on the immune system of mice. J. Nutr. 112: 1747-1755, 1982.
7. BOUNOUS, G., LETOURNEAU, L., KONGSHAVN, P.A.L. Influence of dietary protein type on the immune system of mice. J. Nutr. 113: 1415-1421, 1983.
8. BOUNOUS, G., KONGSHAVN, P.A L. Differential effect of dietary protein type on the B-cell and T-cell immune responses in mice. J. Nutr. 115: 1403-1408, 1985.
9. BOUNOUS, G., SHENOUDA, N., KONGSHAVN, P.A.L., OSMOND, D.G. Mechanism of altered B-cell response induced by changes in dietary protein type in mice. J. Nutr. 115: 1409-1417, 1985.
10. BOUNOUS, G., KONGSHAVN, P.A.L. Influence of protein type in nutritionally adequate diets on the development of immunity. In; *Absorption and utilization of amino acids* N. Friedman, editor, C.R.C. Press, C.R.C. Press, Vol. II, p. 219-233 (1989).
11. EIGEL, W.N., BUTLER, J.E., ERNSTROM, C.A. ET AL. Nomenclature of proteins of cow's milk: Fifth revision. J. Dairy Sci. 67: 1599-1631, 1984.
12. JOHN, A.M., BELL, J.M. Amino acid requirements of the growing mouse. J. Nutr. 106: 1361-1367, 1976.
13. The mouse in biochemical research, Volume III, H.L. Foster, J.D. Small, J.G. Fox, editors, Academic press, p. 58, 1983.
14. HOAG, W.G., DICKIE, M.M. Nutrition in; *Biology of the laboratory mouse*, E.L. Green, editor, McGraw-Hill, New York, pp. 39-43, 1966.
15. CANTANI, A. Latte e siero di latte, in; *Materia medica e terapeutica*, volume I, Vallardi, F. (Publ.), Milano, Italy, p. 385, 1869.
16. SCRIMSHAW, N.S., TAYLOR, C.E., GORDON, J.E. Interactions of nutrition and infection Nutrition 4:13-49, 1988.
17. SCHAEDLER, R.W., DUBOS, R.J. Effect of dietary proteins and amino acids on the susceptibility of mice to bacterial infections. J. Exp. Med 110: 921-934, 1959.
18. JANAS, L.M., PICCIANO, M.F., HATCH, T.F. Indices of protein metabolism in term infants fed human milk, whey-predominant formula, or cow's milk formula. Pediatrics 75: 775-784, 1985.
19. DARLING, P., LEPAGE, G., TREMBLAY, P., COLLET, S., KIEN, L.C., ROY, C.G. Protein quality and quantity in preterm infants receiving the same energy intake. Am. J. Dis. Child. 139: 186-190, 1985.
20. SHENAI, J.P., DAME, M.C., CHURELLA, H.R., REYNOLDS, J.W., BABSON, S.G. Nutritional balance studies in very-low-birth-weight infants: Role of whey formula J. Ped. Gastroent. and Nutr. 5: 428-433, 1986.
21. RAIHA, N.C.R., HEINONEN, K., RASSIN, D.K., GAULL, G.E. Milk protein quantity and quality in low-birthweight infants: I. Metabolic responses and effects on growth. Pediatrics 57: 659-674, 1976.
22. MOSKOWITZ, S.R., PEREIRA, G., SPITZER, A., HEAF, L., AMSEL, J., WATKINS, J.B. Prealbumin as a biochemical marker of nutritional adequacy in premature infants. J. Pediatr. 102: 749-753, 1983.
23. STARLING, E.H. On the absorption of fluids from the connective tissue spaces J. Physiol. (London) 19: 312-326, 1896.
24. SCWARTZ, D.B., DARROW, A.K. Hypoalbuminemia-induced diarrhea in the enterally alimented patients. Nutr. in Clin. Practice 3: 235-237, 1988.
25. BOUNOUS, G. Elemental diets in the prophylaxis and therapy for intestinal lesions: An update. Surgery 105: 571-575, 1989.
26. SHERMAN, P., FORSTNER, J., ROOMI, N., KHATRI, I., FORSTNER, G. Mucin depletion in the intestine of malnourished rats. Am. J. Physiol. 248: G418-G423, 1985.
27. BOUNOUS G., MCARDLE, A.H., HODGES, D.M., GURD, F.N. Biosynthesis of intestinal mucin in shock: Relationship to tryptic hemorrhagic enteritis and permeability to curare. Ann. Surg. 164: 13-22, 1966.
28. BOUNOUS, G. Acute neorosis of the intestinal mucosa: Progress article Gastroenterology 82: 1457-67, 1982.
29. SHAHANI, K.M., AYEBO, A.D. Role of dietary lactobacilli in gastrointestinal microecology. Amer. J. Clin. Nutr. 33: 2448, 1980.
30. PERDIGON, G., deMACIAS, M.E.N., ALVAREZ, S., ET AL. Systemic augmentation of the immune response in mice by feeding fermented milks with *lactobacillus casei* and *lactobacillus acidophilus*. Immunology 63: 17-23, 1988.
31. BOUNOUS, G., KONGSHAVN, P.A.L., GOLD. P. The immunoenhancing property of dietary whey protein concentrate. Clin. Invest. Med. 11: 271-278, 1988.
32. BOUNOUS, G., BATIST, G., GOLD, P. Immunoenhancing effect of dietary whey proteins in mice: role of glutathione. Clin. Invest. Med. 12: 154-161, 1989.
33. MORR, C.V. Functional properties of milk proteins and their use as food ingredients, in; *Developments in dairy chemistry*-1, Appl. Sci. Publ., London, pp. 375-399, 1982.
34. DE WIT, J.N. New approach to the functional characterization of whey proteins for use in food products, in; *Milk proteins* 1984. T.E. Galesloot, B.J. Tinbergen, Pudoc. Wageningen, p. 183-195, 1985.
35. DONOVAN, M., MULVIHILL, D.M. Thermal denaturation and aggregation of whey proteins. Irish J. Food Sci. Tech. 11: 87-100, 1987.
36. KINSELLA, J.E. Milk protein: physicochemioal and funotional properties. C.R.C. Critical review in food science and nutrition, 21: 197-262, 1984.

37. DE WIT, J.N., HONTELEX-BACKX, E. Les proprietes functionelles des proteines du lactoserum; consequences des tratement thermiques. Tech. Lait. 952: 19-22, 1981.
38. LEHNINGER, A.L. Principles of biochemistry. Worth Publ. Inc. p. 688, 1982.
39. DOUGLAS, F.W., GREENBERG, R., FARRELL, H.M., EDMONDSON, L.F. Effects of ultra-high-temperature pasteurization on milk proteins. J. Agri. Food Chem. 29: 11-15, 1981.
40. FARRELL, H.M., DOUGLAS, F.W. Effects of ultra-high-temperature pasteurization on the functional and nutritional properties of milk proteins. Kieler Milchwirtschafl. Forsch. 35: 345-56, 1983.
41. VANAMAN, T.C., BREW, K., HILL, R.L. The disulfide bonds of bovine α-lactalbumin. J. Biol. Chem. 245: 4583-4590, 1970.
42. MEISTER, A., ANDERSON, M.E. Glutathione. Ann. Rev. Bioch. 52: 711-760, 1983.
43. SHVIRO, Y., SHAKLAI, N. Glutathione as a scavenger of free hemin; a mechanism of preventing red cell membrane damage. Biochem. Pharmacol. 36: 3801-3807. 1987.
44. KAPLOWITZ, N., AW, T.Y., OOKHTENS, M. The regulation of hepatic glutathione. Ann. Rev. Pharmacol. Toxicol. 25: 715-744, 1985.
45. ORRENIUS, S., THOR, H., BELLOMO, G., MOLDEUS, P. Glutathione and tissue toxicity. 9th International Congress of Pharmacology, London, July 30th-August 3rd, 1984. W. Patton, J. Mitchell (eds.), McMillan Press (Publ.) p. 57-66, 1984.
46. NOELLE, R.J., LAWRENCE, D.A. Determination of glutathione in lymphocytes and possible association of redox state and proliferative capacity of lymphocytes. Biochem. J. 198: 571-579, 1981.
47. FIDELUS, R.K., TSAN, M.-F. Enhancement of intracellular glutathione promotes lymphocyte activation by mitogen. Cell. Immunol. 97: 155-163, 1986.
48. BOUNOUS, G., BATIST, G., GOLD, P. Immuno-enhancing property of dietary whey protein in mice: Role of glutathione. Clin. Invest. Med 12: 154-161, 1989.
VOS, O., ROOS-VERHEY, W.S.D. Endogenous versus exogenous thiols in radioprotection. Pharmac. Ther. 39: 169-177, 1988.
50. TAYLOR, Y.C., BROWN, J.M. Elevation of intracellular glutathione levels following depletion and its relationship to protection against radiation and alkylating agents. Pharmac. Ther. 39: 293-299, 1988.
51. MEGAW, J.M. Glutathione and ocular photobiology Current Eye Res. 3: 83-87, 1984.
52. CALVIN, H.I., MEDVEDOVSKY, C., WORGUL, B.V. Near-total glutathione depletion and age-specific cataracts induced by Buthionine Sulfoximine in mice. Science 233: 553-555, 1986.
53. AMES, B.N. Food constituents as a source of mutagens, carcinogens, and anticarcinogens. Prog. Clin. Biol. Res. 206: 3-32, 1986.
54. HARMAN, D. Free radicals in aging. Molec. and Cell Bioch. 84: 155-161, 1988.
55. BLUMBERG, J.B , MEYDANI, S N Role of dietary antioxidants in aging, In; *Nutrition and Aging*, M.L. Hutchinson, H.N. Munro, (eds.), Academic Press, New York, p. 85-97, 1986.
56. HAZELTON, G.A., LANG, C.A. Glutathione contents of tissues in the aging mouse. Biochem. J. 188: 25-30, 1980.
57. FAROOQUI, M.Y.H., DAY, W.W., ZAMORANO, D.M. Glutathione and lipid peroxidation in the aging rat. Comp. Biochem. Physiol. 88B: 177-180, 1987.
58. B. HARDING, J.J. Free and protein-bound glutathione in normal and cataraotous human lenses. Biochem. J. 117: 957-960, 1970.
59. WALLER, H.B., BIRKE, G., TIGGS, F.J., BENOHR, H. Glutathiongehalt und glutathion reduzierende enzyme in erithrocyten verschiendenen. Alters. Klin. Wochenchr. 52: 179-184, 1974.
60. HONDA, S., MATSUO, M. Relationships between the cellular glutathione level and in vitro lifespan of human diploid fibroblasts. Exp. Gerontol. 23: 81-86, 1988.
61. AL-TURK, W.A., STOHS, S.J., EL-RASHIDY, F.H., OTHMAN, S. Changes in glutathione and its metabolizing enzymes in human erythrocytes and lymphocytes with age. J. Pharm. Pharmacol. 39: 13-16, 1987.
62. TATEISHI, N., HIGASHI T. SHINYA S., NARUSE. A., SAKAMOTO, Y. Studies on the regulation of glutathione level in rat liver. J. Biochem. 75: 93-103, 1974.
63. MEISTER, A. New aspects of glutathione biochemistry and transport. Selective alteration of glutathione metabolism. Nutr. Rev. 42: 397-410, 1984.
64. GLATT, H., PROTIC-SABLGIC, M., OESCH, F. Mutagenicity of glutathione and cysteine in the Ames Test. Science 220: 961-962, 1983.
65. ESTRELA. J.M., SAEZ. G.T., SUCH, L., VINA, J. The effect of cysteine and N-acetylcysteine on rat liver glutathione (GSH). Biochem. Pharmacol. 32: 3483-3485, 1983.
66. WILLIAMSON, J.M., MEISTER, A. Stimulation of hepatic glutathione formation by administration of L-2-oxothiazolidine-4-carboxylate, a 5- oxo-L-prolinase substrate. Proc. Natl. Acad. Sci. U.S.A. 78: 936-939, 1981.
67. ANDERSON, M.E., MEISTER, A. Transport and direct utilization of gamma-glutamylcyst(e)ine for glutathione synthesis. Proc. Natl. Acad. Sci. U.S.A. 80: 707-711, 1983.
68. PURI, R.N., MEISTER, A. Transport of glutathione as gamma-glutamyloysteinyl-glyoylester, into liver and kidney. Proc. Natl. Acad. Sci. U.S.A. 80: 5258-5260, 1983.
69. WILLIAMSON, J.M., BOETTCHER, B., MEISTER, A. Intracellular cysteine delivery system that protects against toxicity by promoting GSH synthesis. Proc. Natl. Acad. Sci. U.S.A. 79: 6246-6249, 1982.
70. TAYLOR, Y.C., BROWN, J.M. Elevation of intracellular glutathione levels following depletion and its relationship to protection against radiation and alkylating agents. Pharmacol. Ther. 39: 293-299, 1988.
71. WHITE, C.W., JACKSON, J.H., McMURTRY, I.F., REPINE, J.E. Hypoxia increases glutathione redox cycle and protects rat lungs against oxidants. J. Appl. Physiol. 65: 2607-2616, 1988.
72. ANDERSON, M.E. Tissue glutathione: In; *Handbook of methods for oxygen radical research*. C.R.C. Press, 317-329, 1985.
73. RICHIE, J.P., MILLS, B.J., LANG, C.A. Correction of a glutathione defiency in the aging mosquito increases its longevity. Proc. Soc. Exp. Biol. Med. 184: 113-117, 1987.

74. FERNANDEZ-CHECA, J.C., OOKHTENS, M., KAPLOWITZ. Effects of chronic ethanol feeding on rat hepatocyte glutathione. J. Clin. Invest. 83: 1247-1252, 1989.
75. LAUTERBURG, B.H., MITCHELL, J.R. Therapeutic doses of acetaminophen stimulate the turnover of cysteine and glutathione in man. J. Hepatol 4: 206-211, 1987.
76. MEKHAIL-ISHAK, K., HUDSON, N., TSAO, M.S., BATIST, G. Drug metabolizing enzymes in human colon cancer Implications for therapy. Cancer Res. (In press), 1989.
77. LEWIS, A.D., HICKSON, I.D., ROBSON, C.N., HARRIS, A.L., ET AL. P.N.A.S. 85: 8511-8515, 1988.
78. HAMILTON, T.C., WINKLER, M.A., LOUIE, K.G., BATIST, G., ET AL. Augmentation of adriamycin, melphalan and cisplastin cytoxicity in drug resistant and sensitive human ovarian cancer cell lines by BSO mediated GSH depletion. Biochem. Pharm. 34: 2583-2586, 1985.
79. SUZUKAKE, K., VISTICA, B.P., VISTICA, D.T. Dechlorination of L- phenylalanine mustard by sensitive and resistant tumor cells and its relationship to intracellular glutathione content. Biochem. Pharm. 32: 165-171, 1983.
80. ROUS, P. The influence of diet on transplanted and spontaneous mouse tumors. J. Exper. Med. 20: 433-451, 1914.
81. WHITE, R.F., BELKIN, M. Source of tumor proteins. Effect of a low- nitrogen diet on the establishment and growth of a transplanted tumor J. Natl. Cancer Inst. 5: 261-263, 1945.
82. NEWBERNE, P.M., CONNER, M.W. Dietary modifiers of cancer, in; Nutrition, Growth and Cancer. pp. 105-129, Alan R. Riss, Inc., 1988.
83. HAWRYLEWICZ, E.J., HUANG, H.H., LIU, J.M. Dietary protein, enhancement of N-nitrosomethylurea-induced
mammary carcinogenesis. and their effect on hormone regulation in rats. Cancer Res. 46: 4395-43 99, 1986.
84. VISEK, W.J. Dietary protein and experimental carcinogenesis. Adv. Exp. Biol. 206: 163-186, 1986.
85. JACQUET, J., HUYNH, C.H., SAINT, S. Nutrition et cancer experimental: cas du lait C.R. Hebd. Seanc. Acad. Agric. de France. 54: 112-120, 1968.
86. HIRAYAMA, T. An epidemiological study on the effect of diet, especially of milk on the incidence of stomach cancer. Abstr. 9th Int. Cancer Congress, Tokyo, Japan, 713, 1966.
87. IARC International Microecology Group. Dietary fibre, transit- time, fecal bacteria, steroids, and colon cancer in two Scandinavian populations. Lancet II 207-211, 1977.
88. REDDY, G.V., FRIEND, B.A., SHAHANI, K.M., AND FARMER, R.E. Antitumor activity of yogurt components. J. Food Protect. 46: 8-11, 1983.
89. NUTTER, R.L., GRIDLEY, D.S., KETTERING, J.D., ANDRES, M.L., APRECIO, R.M., SLATER, J.M. Modifioation of a transplantable colon tumor and immune responses in mice fed different sources of protein, fat and carbohydrate. Cancer Letters 18: 49-62, 1983.
90. GRIDLEY, D.S., KETTERING, J.D., GARAZA, C.D., ANDRES, M.L., SLATER, J.M., NUTTER, R.L. Modifioation of herpes 2-transformed cell-induced tumors in mice fed different sources of protein, fat and carbohydrate. Cancer Letters 17: 161-173, 1982.
91. NUTTER, R.L., GRIDLEY, D.S., KETTERING, J.D., GOUDE, A.G., SLATER, J.M. BALB/c mice fed milk or beef protein: Differences in response to 1,2-dimethylhydrazine carcinogenesis J.N.C.I. 71: 867-874, 1983.
92. TSURU, S., SHINOMIYA, N., TANIGUCHI, M., SHIMAZAKI, H., TANIGAWA, K., AND NOMOTO, K. Inhibition of tumor growth by dairy products. J. Clin. Lab. Immunol. 25: 177-183, 1988.
93. ENKER, W.E., JACOBITZ, J.L. Experimental carcinogenesis of the colon induced by 1,2-dimethylhydrazine-di HCl: Value as a model of human disease. J. Surg. Res. 21: 291-299, 1976.
CORBETT, T.H., GRISWOLD, D.P., ROBERTS, G.J. ET AL. Evaluation of a single agent and combination of chemotherapeutic agents in mouse colon carcinogenesis. Cancer 40: 2650-2680, 1977.
95. WALSTRA, P., JENNES. Dairy chemistry and physics. Wiley J. Nitork, (ed.), p. 106, 1984.
96. SWAISGOOD, M.E. Characteristics of edible fluids of animal origin: Milk, in; Food Chemistry, O.R. Fennema, (ed.)., Marcel Dekker, p. 796, 1985.
96. KIRKPATRICK, K., WALKER, N.J. Casein and caseinates: Manufacture and utilization in; Milk proteins "84", pp. 196-205, T.E. Galesloot, B.J. Tinbergen, (eds.), Pudoc wageningen, Publishers, 1985.
98. IYNGRARAN, N., YADAV, M. Food allergy, in; Immunopathology of the small intestine. M.N. Marsh (ed.), Wiley, J., p. 418, 1987.
99. AMOURIC, M., MARVALDI, J., PICHON, J., BELLOT, F., FIGARELLA, C. Effect of lactoferrin on the growth of a human colon adenocarcinoma cell line. Comparison with transferrin. In Vitro 20: 543-548, 1984.
100. GURR, M.I. Review of the progress of dairy science: Human and artificial milks for infant feeding. J. Dairy Res. 48: 519-554, 1981.
101. CUNNINGHAM, A., and SZENBERG, A. Further improvements in the plaque technique for detecting single antibody forming cells. Immunology Vol 14, pg. 559-600, (1968).

The embodiments of the invention in which an exclusive property of privilege is claimed are defined as follows:

1. A whey protein composition comprising an undenatured whey protein concentrate obtained from raw bovine, goat or sheep milk which contains substantially all the heat labile whey protein present in the raw milk, the whey protein being present in an amount sufficient to provide an amount of from about 18 to about 28 grams of whey protein per 100 grams of composition, Vitamin $B_1$ in an amount of at least 1.5 mg per 100 grams of composition and Vitamin $B_2$ in an amount of at least 1.5 mg per 100 grams of composition.

2. The composition as in claim 1, wherein the amount of Vitamin $B_1$ is in the range of from 1.5 mg to 2.0 mg per 100 g of composition.

3. The composition as in claim 1, wherein the amount of Vitamin $B_2$ is in the range of from 1.5 mg to 2.0 mg per 100 g of composition.

4. The composition as in claim 1, wherein the composition is free of lactose.

5. The composition as in claim 1 having immunoenhancing properties that are heat labile, insensitive to pancreatic digestion and dependent upon the undenatured state.

6. A method of improving the immune response in mammals as measured by sheep red blood cell injection comprising administering orally to the mammal an undenatured whey protein concentrate obtained from bovine, goat or sheep milk containing substantially all the heat labile whey protein present in the raw milk, the whey protein being present in an amount sufficient to provide an amount of from about 18 g to about 28 g of whey protein per 100 g of composition, Vitamin $B_1$ in an amount of at least 1.5 mg per 100 grams of composition and Vitamin $B_2$ in an amount of at least 1.5 mg per 100 grams of composition, the Vitamin $B_1$ and Vitamin $B_2$ being administered in amounts in excess of minimum daily requirements.

7. The method as in claim 6, wherein the amount of Vitamin $B_1$ is an amount of from 1.5 mg to 2.0 mg per 100 g of composition.

8. The method as in claim 6, wherein the amount of Vitamin $B_2$ is an amount of from 1.5 mg to 2.0 mg per 100 g of composition.

9. The method as in claim 6, wherein the minimum daily requirement of Vitamin $B_1$ is 0.5-0.6 mg per 1000 calorie.

10. The method as in claim 6, wherein the minimum daily requirement of Vitamin $B_2$ is 1.2-1.5 mg per day.

11. The method as in claim 6, wherein the minimum daily requirement of Vitamin $B_1$ is 0.5 milligrams per 1000 calorie and the minimum daily requirement for Vitamin $B_2$ is 0.5-0.6 milligrams per 1000 calorie or 1.2-1.5 milligrams per day.

12. A method of improving the immune response in mammals as measured by sheep red blood cell injection comprising the step of administering to a mammal a composition comprising Vitamin $B_2$ in an amount in excess of minimum daily requirements, and an undenatured whey protein concentrate containing substantially all the heat labile whey protein present in the raw milk in an amount sufficient substantially to satisfy the daily requirements of protein of said mammal.

13. A method of improving the immune response in mammals as measured by sheep red blood cell injection comprising the step of administering to the mammal an undenatured whey protein concentrate containing substantially all the heat labile whey protein present in the raw milk, said whey protein concentrate having immunoenhancing properties that are heat labile, insensitive to pancreatic digestion and dependent upon the undenatured state and being administered in an amount substantially sufficient to satisfy requirements of protein of said mammal.

* * * * *